(12) United States Patent
Tsai et al.

(10) Patent No.: US 10,897,894 B2
(45) Date of Patent: Jan. 26, 2021

(54) METHODS OF AND SYSTEM FOR GENERATING ANTIMICROBIAL WIPES

(71) Applicant: GOJO Industries, Inc., Akron, OH (US)

(72) Inventors: Tsung-Chan Tsai, Worthington, OH (US); Jeffrey S. Louis, Akron, OH (US); Daphne Pappas Antonakas, Hudson, OH (US); Sameer Kalghatgi, Cherry Hill, NJ (US); Robert L. Gray, Kent, OH (US)

(73) Assignee: GOJO Industries, Inc., Akron, OH (US)

( * ) Notice: Subject to any disclaimer, the term of this patent is extended or adjusted under 35 U.S.C. 154(b) by 129 days.

(21) Appl. No.: 15/753,565

(22) PCT Filed: Aug. 30, 2016

(86) PCT No.: PCT/US2016/049375
§ 371 (c)(1),
(2) Date: Feb. 20, 2018

(87) PCT Pub. No.: WO2017/040463
PCT Pub. Date: Mar. 9, 2017

(65) Prior Publication Data
US 2018/0242577 A1 Aug. 30, 2018

Related U.S. Application Data

(60) Provisional application No. 62/211,967, filed on Aug. 31, 2015.

(51) Int. Cl.
*A01N 25/34* (2006.01)
*H05H 1/24* (2006.01)
(Continued)

(52) U.S. Cl.
CPC ............. *A01N 25/34* (2013.01); *A01N 25/00* (2013.01); *A61L 2/18* (2013.01); *C02F 1/4608* (2013.01);
(Continued)

(58) Field of Classification Search
CPC .......... A01N 25/34; A01N 25/00; A61L 2/18; A61L 2202/11; A61L 2202/14;
(Continued)

(56) References Cited

U.S. PATENT DOCUMENTS 3,918,987 A 11/1975 Kopfer
4,020,856 A 5/1977 Materson
(Continued)

FOREIGN PATENT DOCUMENTS

EP 1356828 5/2007
WO 2001010215 2/2001
(Continued)

OTHER PUBLICATIONS

International Search Report and Written Opinion from International Application No. PCT/US2013/063360, dated Dec. 11, 2013.
(Continued)

*Primary Examiner* — Xiuyu Tai
(74) *Attorney, Agent, or Firm* — Calfee, Halter & Griswold LLP

(57) ABSTRACT

Exemplary methods of and system for generating an antimicrobial wipe to clean and disinfect a surface contaminated with bacteria, viruses, spores, fungi, or combinations thereof. In some embodiments, the method includes applying non-thermal plasma to a moistened wipe to activate a liquid in the wipe. In some embodiments, the method includes applying non-thermal plasma to a liquid and then applying the activated liquid to a wipe. In one embodiment of a system for generating an antimicrobial wipe the system
(Continued)

US 10,897,894 B2

Page 2 includes a housing having an opening; a supply of wipes disposed within the housing; a non-thermal plasma generator disposed within the housing; a power supply electrically coupled to the non-thermal plasma generator; and a feed system disposed within the housing, wherein the feed system moves one or more wipes from the supply of wipes past the plasma generator and out of the opening. As the feed system moves the wipes past the plasma generator, the plasma generator applies non-thermal plasma to the wipes.

20 Claims, 17 Drawing Sheets

(51) Int. Cl.
| | |
|---|---|
| A61L 2/18 | (2006.01) |
| C02F 1/46 | (2006.01) |
| A01N 25/00 | (2006.01) |
| A61L 2/00 | (2006.01) |
| A61L 2/14 | (2006.01) |

(52) U.S. Cl.
CPC ............ H05H 1/24 (2013.01); H05H 1/2406 (2013.01); A61L 2/0011 (2013.01); A61L 2/0088 (2013.01); A61L 2/14 (2013.01); A61L 2202/11 (2013.01); A61L 2202/14 (2013.01); A61L 2202/15 (2013.01); A61L 2202/17 (2013.01); C02F 2303/04 (2013.01); C02F 2305/023 (2013.01); H05H 2001/2412 (2013.01); H05H 2240/20 (2013.01); H05H 2245/1225 (2013.01)

(58) Field of Classification Search
CPC .... A61L 2202/15; A61L 2/14; A61L 2202/17; A61L 2/186; A61L 2/0011; A61L 2/0088; H05H 1/2406; H05H 2001/2412; H05H 2240/20; H05H 1/24; H05H 1/0011; H05H 2245/1225; C02F 1/4608; C02F 2303/04; C02F 2305/023; D06M 10/025; D06M 10/10; D06M 13/463; D06M 14/32; D06M 23/02; D06M 10/08; D06M 16/00; D06M 10/04; D06M 23/12; D06M 14/18; D06M 14/26; D06M 13/477; C11D 17/049; D06B 19/00; A47L 13/16; Y10T 428/249953; Y10T 428/31504

See application file for complete search history.

(56) References Cited

U.S. PATENT DOCUMENTS

| | | | |
|---|---|---|---|
| 5,281,315 A | 1/1994 | Krapivina et al. | |
| 5,872,359 A | 2/1999 | Stewart | |
| 5,876,663 A | 3/1999 | Laroussi | |
| 5,920,799 A | 7/1999 | Graves | |
| 6,030,506 A | 2/2000 | Bittenson et al. | |
| 6,171,625 B1 | 1/2001 | Denvir et al. | |
| 6,176,941 B1 | 1/2001 | Jewett et al. | |
| 6,387,238 B1 | 5/2002 | Merk | |
| 6,543,460 B1 | 4/2003 | Denes et al. | |
| 6,706,243 B1 | 3/2004 | Sias et al. | |
| 6,723,091 B2 | 4/2004 | Goble et al. | |
| 6,875,399 B2 | 4/2005 | McVey | |
| 6,911,225 B2 | 6/2005 | Ruan et al. | |
| 6,969,487 B1 | 11/2005 | Sias | |
| 7,004,356 B1 | 2/2006 | Sayers | |
| 7,008,592 B2 | 3/2006 | Sias et al. | |
| 7,163,664 B2 | 1/2007 | Paskalov et al. | |
| 7,291,314 B2 | 11/2007 | Paskalov et al. | |
| 7,326,382 B2 | 2/2008 | Adiga et al. | |
| 7,326,383 B2 | 2/2008 | Gunter et al. | |
| 7,569,203 B2 | 8/2009 | Fridman et al. | |
| 7,608,839 B2 | 10/2009 | Coulombe et al. | |
| 7,829,051 B2 | 11/2010 | Fridman et al. | |
| 7,989,673 B2 | 8/2011 | Paskalov et al. | |
| 8,048,930 B2 | 11/2011 | Bobbert | |
| 8,354,057 B2 | 1/2013 | Heselton et al. | |
| 8,383,036 B2 | 2/2013 | Sloan et al. | |
| 8,388,618 B2 | 3/2013 | Fridman et al. | |
| 9,339,572 B2 | 5/2016 | Tsai et al. | |
| 9,550,007 B2 | 1/2017 | Tsai et al. | |
| 9,662,412 B2 | 5/2017 | Ferrell et al. | |
| 2003/0132100 A1 | 7/2003 | Crowe et al. | |
| 2004/0120844 A1 | 6/2004 | Tribelsky et al. | |
| 2004/0216845 A1 | 11/2004 | Golkowski | |
| 2006/0189976 A1 | 8/2006 | Karni et al. | |
| 2006/0223729 A1 | 10/2006 | Hamblin et al. | |
| 2006/0229225 A1 | 10/2006 | Martin | |
| 2007/0202315 A1* | 8/2007 | Duffield | A47L 13/16 428/304.4 |
| 2007/0251953 A1 | 11/2007 | Criswell et al. | |
| 2008/0118734 A1 | 5/2008 | Goodwin | |
| 2009/0041617 A1 | 2/2009 | Lee | |
| 2009/0054896 A1 | 2/2009 | Fridman et al. | |
| 2009/0175956 A1 | 7/2009 | Buschmann et al. | |
| 2010/0145253 A1 | 6/2010 | Gutsol et al. | |
| 2010/0168499 A1 | 7/2010 | Gutsol et al. | |
| 2010/0196505 A1 | 8/2010 | Kaiser et al. | |
| 2010/0209293 A1 | 8/2010 | Ikawa et al. | |
| 2010/0280513 A1 | 11/2010 | Juergen et al. | |
| 2010/0296977 A1 | 11/2010 | Hancock | |
| 2011/0112528 A1 | 5/2011 | Stieber et al. | |
| 2011/0171188 A1 | 7/2011 | Morfill et al. | |
| 2011/0251604 A1 | 10/2011 | Staack et al. | |
| 2012/0039747 A1 | 2/2012 | Morfill et al. | |
| 2012/0042419 A1 | 2/2012 | Wilson et al. | |
| 2012/0100037 A1 | 4/2012 | Shannon et al. | |
| 2012/0305787 A1 | 12/2012 | Henson | |
| 2012/0315684 A1 | 12/2012 | Hayashi et al. | |
| 2014/0003998 A1* | 1/2014 | Franklin | A61L 2/14 422/29 |
| 2014/0100277 A1 | 4/2014 | Gray et al. | |
| 2014/0271354 A1 | 9/2014 | Tsai | |
| 2014/0322096 A1 | 10/2014 | Pelfrey et al. | |
| 2015/0038584 A1 | 2/2015 | Fridman | |
| 2015/0306258 A1 | 10/2015 | Ferrell | |
| 2016/0051713 A1 | 2/2016 | Robert | |
| 2016/0166607 A1 | 6/2016 | Roe | |
| 2016/0367712 A1 | 12/2016 | Robert | |

FOREIGN PATENT DOCUMENTS

| | | |
|---|---|---|
| WO | 2002059046 | 8/2002 |
| WO | 2005123891 A2 | 12/2005 |
| WO | 2006116252 | 4/2006 |
| WO | 2006076334 | 7/2006 |
| WO | 2007048806 | 5/2007 |
| WO | 2007063987 | 6/2007 |
| WO | 2010009103 | 1/2010 |
| WO | 2010022160 | 2/2010 |
| WO | 2010085513 | 7/2010 |
| WO | 2010107722 | 9/2010 |
| WO | 2010107741 | 9/2010 |
| WO | 2010107744 | 9/2010 |
| WO | 2010107745 | 9/2010 |
| WO | 2010107746 | 9/2010 |
| WO | 2012018891 | 2/2012 |
| WO | 2012112042 | 8/2012 |
| WO | 2014145570 | 9/2014 |

OTHER PUBLICATIONS

International Search Report and Written Opinion from International Application No. PCT/US2014/030361, dated Jul. 16, 2014.
International Search Report and Written Opinion from PCT/US2016/044160, dated Jan. 19, 2017.
Office Action from European Application No. 14724869.4 dated Oct. 31, 2016.

(56) References Cited

OTHER PUBLICATIONS

Alekseev et al., "Nonthermal Dielectric Barrier Discharge (DBD) Plasma Suppresses Herpes Simplex Virus Type 1 (HSV-1) Replication in Corneal Epithelium", TVST, 2014, vol. 3, No. 2, Article 2, pp. 1-14.

Alhabshan et al., "Effects of In-vivo Application of Cold Atmospheric Plasma on Corneal Wound Healing in New Zealand White Rabbits", International Journal of Ophthalmic Pathology, 2013, 2:3, pp. 1-5.

Andrade et al., A new, versatile, direct-current helium atmospheric-pressure glow discharge. Journal of Analytical Atomic Spectrometry, 2006. 21(11): p. 1175-1184.

Blajan, et al., Emission spectroscopy of pulsed powered microplasma for surface treatment of PEN film. Industry Applications, IEEE Transactions on, 2011, 47(3): p. 1100-1108.

Bruggeman et al., Non-thermal plasmas in and in contact with liquids. Journal of Physics D: Applied Physics, 2009. 42 (5): p. 053001.

Brun et al., "Disinfection of Ocular Cells and Tissues by Atmospheric-Pressure Cold Plasma", PLoS One, Mar. 2012, vol. 7, Issue 3, e33245, pp. 1-13.

Burlica et al. "Formation of H2 and H202 in a Water-Spray Gliding Arc Nonthermal Plasma Reactor", Industrial & Engineering Chemistry Research, vol. 49, No. 14, Jun. 24, 2010.

Cabiscol et al., Oxidative stress in bacteria and protein damage by reactive oxygen species. International Microbiology, 2010. 3(1): p. 3-8.

Critzer et al., "Atmospheric Plasma Inactivation of Foodborne Pathogens on Fresh Produce Surfaces", Journal of Food Protection, vol. 70, No. 10, 2007, pp. 2290-2296.

Danil et al., Cold Plasma Inactivation of Bacillus Cereus and Bacilus Antracis (Anthrax) Spores, IEEE Service Center, Piscataway NJ, US vol. 38, No. 8, Aug. 1, 2010, pp. 1878-1884.

Daifas et al., Effect of ethanol vapor on growth and toxin production by Clostridium botulinum in a high moisture bakery product. Journal of food safety, 2000. 20(2): p. 111-125.

Ermolaeva et al., "Bactericidal effects of non-thermal argon plasma . . . ", J. Med. Microbiol., Sep. 2010, http://jmm.sgmjournals.org/content/60/1/75.full.

Escobar-Cortes et al., "Proteases and sonication specifically remove the exosporium layer . . . ", J. Microbiol. Methods, Jan. 2013.

Gaunt et al., Bactericidal action of the reactive species produced by gas-discharge nonthermal plasma at atmospheric pressure: a review. Plasma Science, IEEE Transactions on, 2006. 34(4): p. 1257-1269.

Gil et al., Fresh-cut product sanitation and wash water disinfection: problems and solutions. International journal of food microbiology, 2009. 134(1): p. 37-45.

Hayashi et al., Sterilization of medical equipment using radicals produced by oxygen/water vapor RF plasma. Japanese journal of applied physics, 2006. 45(10S): p. 8358.

Huang, "Non-thermal Plasma Inactivation of Bacillus Amyloliquefaciens Spores", Master's Thesis, Univ. of Tennessee, 2011, http://www.trace.tennessee.edu/utk.sub.--gradthes/980.

Joshi, S.G., et al., Nonthermal dielectric-barrier discharge plasma-induced inactivation involves oxidative DNA damage and membrane lipid peroxidation in *Escherichia coli*. Antimicrobial agents and chemotherapy, 2011. 55(3): p. 1053-1062.

Klampfl, T.G., et al., Cold atmospheric air plasma sterilization against spores and other microorganisms of clinical Interest. Applied and Environmental Microbiology, 2012. 78(15): p. 5077-5082.

Klimpel, Clostridium Difficle Test Exposure to BIT Plasma, Plasma Clostridium Difficile Killing Trials, 2009 (5 pages).

Laroussi, M. and F. Leipold, Evaluation of the roles of reactive species, heat, and UV radiation in the inactivation of bacterial cells by air plasmas at atmospheric pressure. International Journal of Mass Spectrometry, 2004. 233(1): p. 81-86.

Lawley et al., "Proteomic and Genomic Characterization of Highly Infectious . . . ", J. Bacteriol. 2009, vol. 191, No. 17, pp. 5377-5386, Jun. 2009, http://jb.asm.org/content/191/1715377.

Lawley et al., "Use of Purified Clostridium difficile Spores . . . ", Appl. Environ. Microbiol., pp. 6895-6900, Aug. 2010.

Lerouge et al., Plasma sterilization: a review of parameters, mechanisms, and limitations. Plasmas and Polymers, 2001. 6(3): p. 175-188.

Lukes et al., Aqueous-phase chemistry and bactericidal effects from an air discharge plasma in contact with water: evidence for the formation of peroxynitrite through a pseudo-second-order post-discharge reaction of H2O2 and HNO2. Plasma Sources Science and Technology, 2014. 23(1): p. 015019.

Machala et al., Formation of ROS and RNS in Water Electro-Sprayed through Transient Spark Discharge in Air and their Bactericidal Effects. Plasma Processes and Polymers, 2013. 10(7): p. 649-659.

Matthes et al., Antimicrobial Efficacy of Two Surface Barrier Discharges with Air Plasma against In Vitro Biofilms. PloS one, 2013. 8(7): p. e70462.

Misra et al., Nonthermal plasma inactivation of food-borne pathogens. Food Engineering Reviews, 2011. 3(3-4): p. 159-170.

Oehmigen et al., "The Role of Acidification for Antimicrobial . . . ", Wiley InterScience, Plasma Process. and Polym. 2010, 7, pp. 250-257, 2010.

Niemira, Cold Plasma Inactivates *Salmonella* Stanley and *Escherichia coli* O157:h7 Inoculated on Golden Delicious Apples, Journal of Food Protection, vol. 71, No. 7, 2008, pp. 1357-1365.

Niemira, Cold Plasma Decontamination of Foods. Annual Review of Food Science and Technology, 2012. 3: p. 125-142.

Pankaj et al., Applications of cold plasma technology in food packaging. Trends in Food Science & Technology, 2014. 35(1): p. 5-17.

Pappas, Status and potential of atmospheric plasma processing of materials. Journal of Vacuum Science & Technology A, 2011. 29(2): p. 020801.

Paredes-Sabja, et al., "Adherence of Clostridium difficile spores to Caco-2 cells in culture", J. Med. Microbiol., pp. 1208-1218, 2012.

Park et al., "Reactive nitrogen species produced in water by non-equilibrium plasma increase plant growth rate and nutritional yield", Current Applied Physics 13 (2013), pp. 519-529.

Pei et al., "Inactivation of a 25.5 . . . Enterococcus faecalis biofilm . . . ", J. Phys. D: Appl. Phys., http://www.stacks.iop.org/JPhysD/45/165205, Apr. 2012.

Sera et al., "Germination of Chenopodium Album in Response to Microwave Plasma Treatment", Plasma Science and Technology, vol. 10, No. 4, Aug. 2008, pp. 506-511.EA.

Sosnin et al., The effects of UV irradiation and gas plasma treatment on living mammalian cells and bacteria: a comparative approach. Plasma Science, IEEE Transactions on, 2004. 32(4): p. 1544-1550.

Tolls et al., Surface Layers of Clostridium difficile Endospores, J. Bacteriol. 2011, vol. 193, No. 23, pp. 6461-6470, 2011.

Traylor et al., "Long-term antibacterial efficacy of air plasma-activated water", J. Phys. D: Appl. Phys., Nov. 2011, http://www.stacks.iop.org/JPhysD/44/472001.

Tsai et al.,, Rapid Inactivation of Bacterial Spores Using Plasma Activated Water:Development, Species Identification and Sporicidal Mechanism, 22nd Internation Symposium on Plasma Chemistry, Jul. 5, 2015, pp. 1-4.

Utku Ercan et al., Nonequilibrium Plasma-Activated Antimicrobial Solutions are Broad-Spectrum and Retain Their Efficacies for Extended Period of Time, Plasma Processes and Polymers, vol. 10, No. 6, Apr. 12, 2013, pp. 544-555.

Venezia, et al., "Lethal Activity of Nonthermal Plasma . . . ", Univ. of Chicago Press, Infection Control and Hospital Epidemiology, vol. 29, No. 5, May 2008, http://www.jstor.org/stable/10.1086/588003.

Von Woedtke et al., Plasma-liquid interactions: chemistry and antimicrobial effects, in Plasma for Bio-Decontamination, Medicine and Food Security. 2012, Springer. p. 67-78.

Zhu et al., A dc non-thermal atmospheric-pressure plasma microjet. Plasma Sources Science and Technology, 2012. 21(3): p. 034018.

\* cited by examiner

US 10,897,894 B2

METHODS OF AND SYSTEM FOR GENERATING ANTIMICROBIAL WIPES

RELATED APPLICATIONS

This application claims the benefits of and priority to U.S. Provisional Application Ser. No. 62/211,967, titled Methods of and System for Generating Antimicrobial Wipes, and filed on Aug. 31, 2015, and which is incorporated herein in its entirety.

TECHNICAL FIELD

The present invention relates generally to antimicrobial wipes and, more particularly, to a method of and system for generating antimicrobial wipes.

BACKGROUND OF THE INVENTION

Bacteria, viruses, spores, fungi, and combinations thereof can contaminate surfaces and through exposure to humans cause many illnesses and deaths every year. For example, the germ Clostridium difficile, "C. difficile" is linked to 14,000 American deaths each year. Current methods of killing or deactivating C. difficile include applying bleach, liquid solutions containing hydrogen peroxide, and other biocidal compounds, and/or ultraviolet radiation (UV) to C. difficile for a period of time longer than 3 minutes.

SUMMARY OF INVENTION

Exemplary methods of and systems for generating an antimicrobial wipe to clean and disinfect a surface contaminated with bacteria, viruses, spores, fungi, or combinations thereof are disclosed herein. In one exemplary embodiment, the method includes applying non-thermal plasma to a moistened wipe to activate a liquid in the wipe. In another exemplary embodiment, the method includes applying non-thermal plasma to a liquid and then applying the activated liquid to a wipe.

In one embodiment of a system for generating an antimicrobial wipe, the system includes a housing having an opening, a supply of wipes disposed within the housing, a non-thermal plasma generator disposed within the housing, a power supply electrically coupled to the non-thermal plasma generator, and a feed system disposed within the housing, wherein the feed system moves one or more moistened wipes past the plasma generator and out of the opening. As the feed system moves the wipes past the plasma generator, the plasma generator applies non-thermal plasma to the wipes.

In another embodiment of a system for generating an antimicrobial wipe, the system includes a housing having an opening, a supply of wipes disposed within the housing, wipe wetting system disposed within the housing, and a feed system disposed within the housing, wherein the feed system moves one or more wipes from the supply of wipes past the wipe wetting system and out of the opening. As the feed system moves the wipes past the wipe wetting system, the wipe wetting system applies plasma-activated fluid to the wipes.

BRIEF DESCRIPTION OF THE DRAWINGS

These and other features and advantages of the present invention will become better understood with regard to the following description and accompanying drawings in which.

DETAILED DESCRIPTION

Plasmas, or ionized gases, have one or more free electrons that are not bound to an atom or molecule. Plasmas may be generated using a variety of gases including, air, nitrogen, noble gases (He, Ar, Xe, Kr, etc.), oxygen, carbon dioxide and mixtures thereof under a strong electric field. In addition, non-thermal plasmas provide high concentrations of energetic and chemically active species. They can operate far from thermodynamic equilibrium with high concentrations of active species and yet remain at a temperature that is substantially the same as room temperature. The energy from the free electrons may be transferred to additional plasma components creating additional ionization, excitation and/or dissociation. Fluid that is contacted with plasma becomes "activated" and is referred to herein as plasma activated fluid, and in some embodiments, the plasma activated fluid is plasma activated water.

In some embodiments, plasmas may contain superoxide anions [O2.$^-$], which react with H$^+$ in acidic media to form hydroperoxy radicals, HOO.$^{\cdot}$ [O$_2$.$^-$]+[H$^+$]→[HOO.]. Other radical species may include OH$^-$ and NO$^-$ in aqueous phase or the presence of air or gas. Treating water with plasma results in plasma activated water that may contain concentrations of one or more of ozone, H$_2$O$_2$, nitrates, nitrites, peroxynitrious acid, peroxynitrite, hydroxyl radicals and other active species.

Activating water with plasma to obtain plasma activated water is shown and described in U.S. Published Patent Application Number 2014/0322096, titled Sanitization Station Using Plasma Activated Fluid, filed on Jul. 2, 2014 U.S. Published Patent Application Number 2014/0100277, titled Solutions and Methods of Making Solutions to Kill or Deactivate Spores Microorganisms, Bacteria and Fungus, filed on Mar. 15, 2013. Both of which are incorporated by reference herein in their entirety. Several other patents and applications such as: WO 2007/048806, titled Method for the Preparation of Biocidal Activated Water Solutions, filed Oct. 25, 2006; WO 2012/018891, which is titled Materials for Disinfection Produced by Non-Thermal Plasma, filed on Aug. 3, 2011; and U.S. Pat. No. 7,291,314, titled Activated Water Apparatus and Methods, filed Dec. 20, 2001, are incorporated herein by reference in their entirety for their disclosure on activating fluid. Further, U.S. patent Ser. No. 13/843,189, titled Methods and Solutions for Killing or Deactivating Spores, filed Mar. 15, 2013 and U.S. patent Ser. No. 13/838,418, titled Methods and Solutions for Killing or Deactivating Bacteria, filed Mar. 15, 2013 are also incorporated herein by reference in their entirety for their disclosure on activating fluid.

Figure 1:
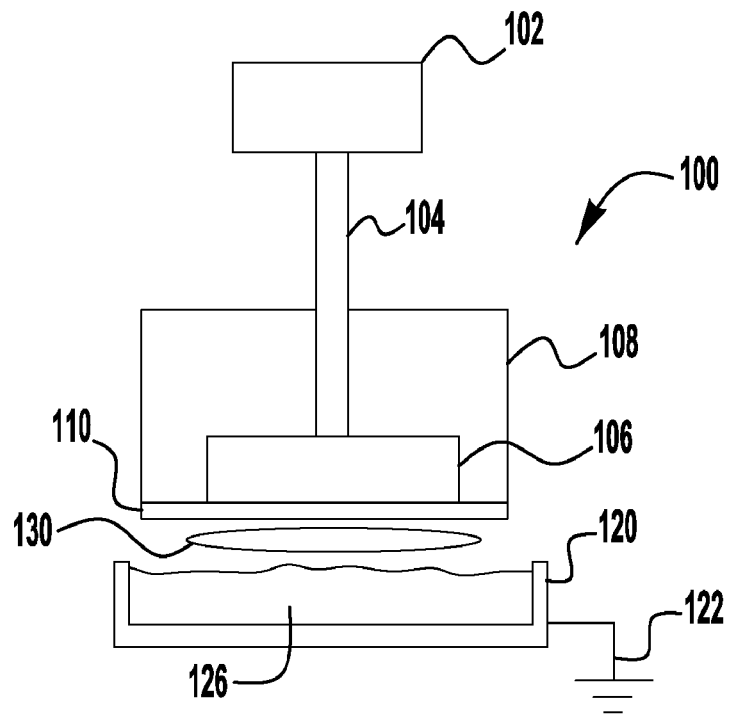
FIG. 1 illustrates a prior art embodiment of a device for creating activated water using direct plasma.

It is known to treat water and other fluids with plasma to "activate" them. One method of activating water and other fluids is illustrated in FIG. 1, which is a prior art dielectric barrier discharge ("DBD") plasma generating system 100. The prior art plasma generating system 100 includes a high voltage source 102, a conductor 104, a housing 108, a high voltage electrode 106 and a dielectric barrier 110. The plasma generating system 100 also includes a container 120 which is grounded with a grounding conductor 122. During operation, the high voltage source 102 is turned on and plasma 130 forms below the dielectric barrier 110. The high voltage power source 102 may be a high frequency AC power source, an RF power source, a pulsed DC power source, a pulsed AC power source, a microwave power source or the like. The power supply can be pulsed with a duty cycle of 0-100% and pulse duration of 1 nanosecond up to 1 microsecond.

The plasma 130 contacts the water or fluid 126 and activates the water or fluid 126. Fluid 126 activated by direct contact with plasma is referred to herein as "direct plasma activated fluid."

Figure 2:
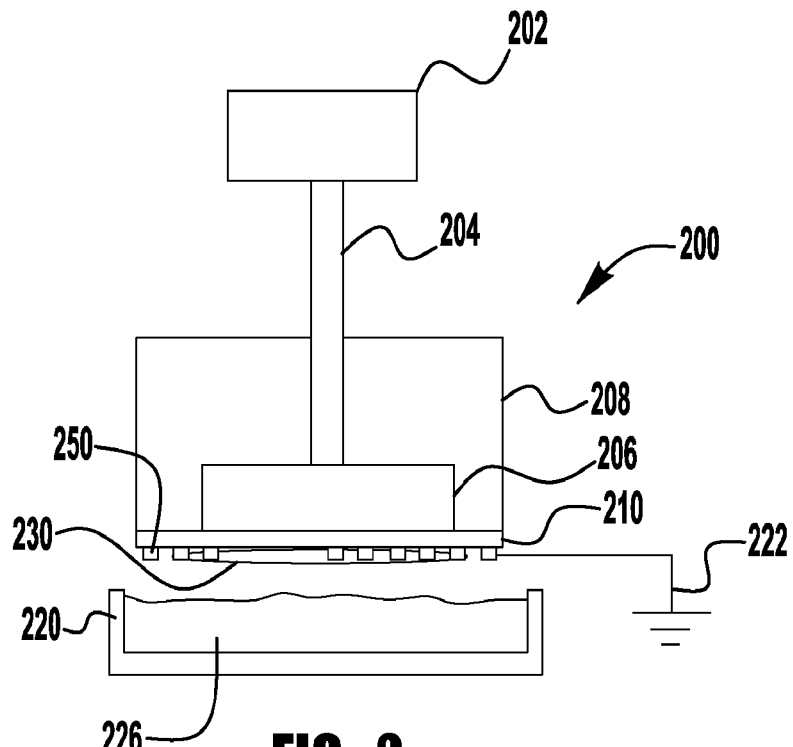
FIG. 2 illustrates a prior art embodiment of a device for creating activated water using indirect plasma.

FIG. 2 illustrates an exemplary prior art system 200 for activating a fluid using indirect plasma. System 200 includes a high voltage power source 202. High voltage power source 202 may be a high frequency AC power source, an RF power source, a microwave power source, a pulsed DC power source, a pulsed AC power source or the like. The power supply can be pulsed with a duty cycle of 0-100% and pulse duration of 1 nanosecond up to 1 microsecond.

The exemplary system 200 includes a housing 208, a high voltage electrode 206 connected to high voltage power source 202 by cable 204. A dielectric barrier 210 is located between high voltage electrode 206 and the fluid 226 that is to be activated. A filter 250 is also included. Filter 250 is a conductive mesh that is grounded by grounding conductor 222.

During operation of system 200, when high voltage electrode 206 is energized, plasma 230 forms between the dielectric barrier 210, and the filter 250 (if the filter 250 is made of a conductive material and grounded) prevents charged ions and electrons from passing through and contacting the fluid 226 to be activated. Thus, only neutral species pass through and activate the fluid 226. This is typically referred to as "afterglow" or "indirect" plasma. In some embodiments, the fluid is water. Fluid 226 activated by the reactive neutral species that passes through, or is created through filter 250, is referred to "indirect plasma activated fluid."

The use of a systems that can generate antimicrobial wipes on demand and on-site and the methods of generating the wipes are disclosed herein. In some embodiments, gas mixtures, water mist or spray, or mist or spray of liquids containing antimicrobial compounds may be used to moisten one or more wipes (e.g. paper towels). In some embodiments, the fluids may be activated via plasma prior to the application on the wipe materials or the wipes may be pre-moistened with the above mentioned fluids and then exposed to plasma. Use of plasma can create a wipe with a localized environment of antimicrobial species. The system and method can be used in multiple application areas including decontamination of hard and soft surfaces by wiping the surfaces with the antimicrobial wipe.

Figure 3:
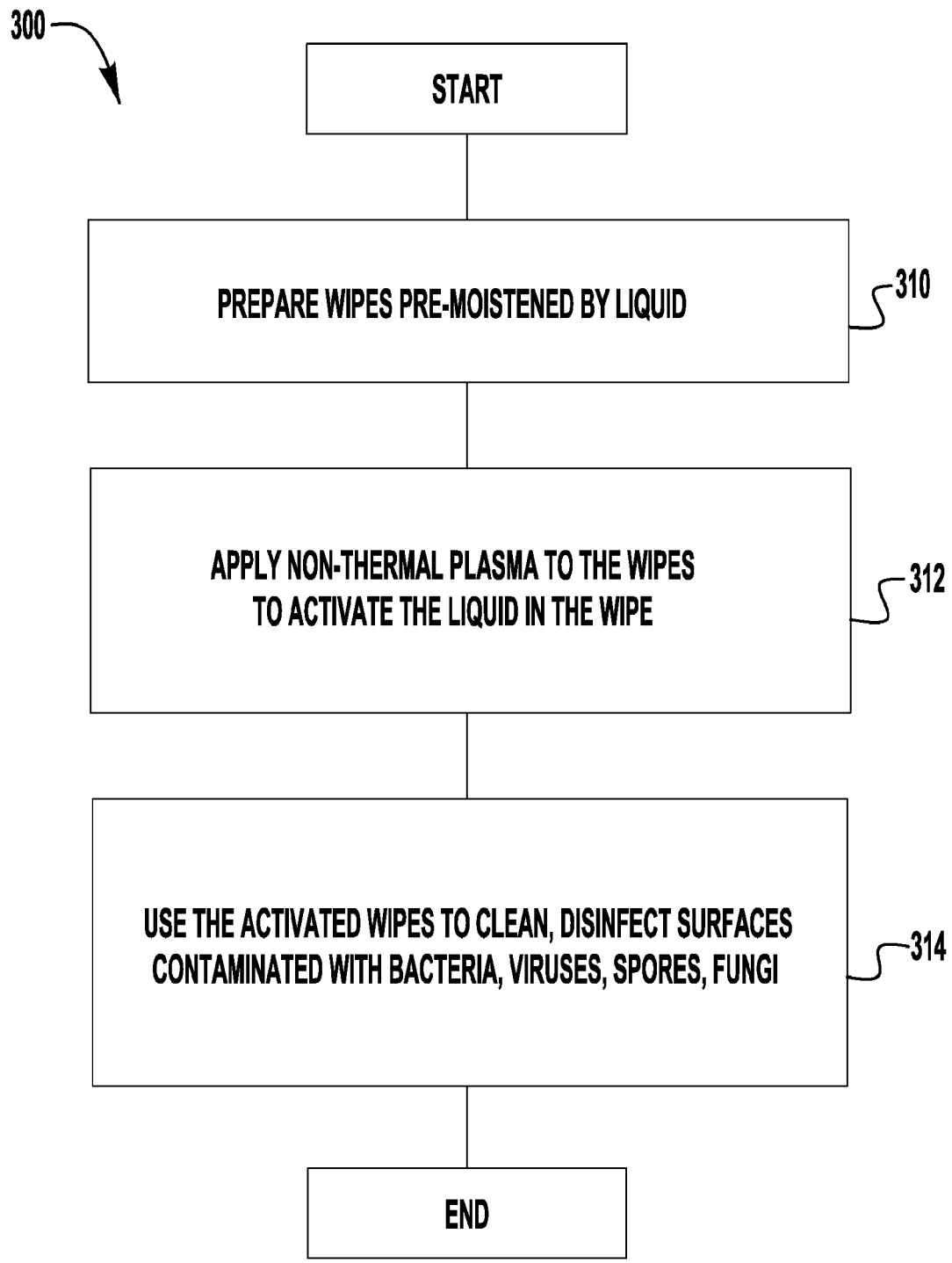
FIG. 3 illustrates an exemplary method for generating antimicrobial wipes.

FIG. 3 illustrates an exemplary method 300 of generating an antimicrobial wipe that can be used to clean and disinfect a surface contaminated with bacteria, viruses, spores, fungi, or combinations thereof. The method 300 includes, as shown in block 310, providing one or more wipes pre-moistened by a liquid and, as shown in block 312, applying non-thermal plasma to the one or more moistened wipes to activate the liquid in the one or more wipes. The activated one or more wipes can be used, as shown in block 314, to wipe down a surface contaminated with bacteria, viruses, spores, fungi, or other contaminants in order to clean, disinfect, and/or sanitize the surface.

The wipe can take a variety of forms. For example, the wipe can be made of a variety of materials. Non-limiting examples of suitable materials include polypropylene, microfiber, polyester, viscose, non-woven fiber, or any other suitable materials and combination thereof. The wipe can be configured in a variety of shapes and sizes. For example, the wipe can be provided as a single layer sheet, a multilayered sheet or multiple sheets. Wipes provided as multiple sheets can be provided as multiple separate sheets or multiple sheets connected or attached together, such as for example, as a c-fold, roll or stack of connected wipes. The connected wipes can be separable. For example, separable wipes may be divided into individual sheets by lines of weakness, such as for example, a perforation line or an area of reduced thickness. In other embodiments, however, the connected wipes may not be divided by lines of weakness, but may be separable by cutting or tearing. Thus, a system implementing the method may have structure to facilitate cutting or tearing the connected wipes, such as for example, a blade or sharp edge. In one exemplary embodiment, each wipe is formed as a separate rectangular or square sheet. In another exemplary embodiment, a plurality of wipes are provided in a roll.

The liquid used to moisten the wipe can be a variety of different liquids. In some exemplary embodiments, the liquid in the wipe can be water or water with additional additives. For example, in one exemplary embodiment, the liquid can be an alcohol, such as ethyl alcohol (ethanol) or isopropanol alcohol, diluted with water. Exemplary embodiments include formulations that contains water and ethanol mixtures. These formulations may contain up to about 70% ethanol, including up to about 60% ethanol, including up to about 50% ethanol, including up to about 40% ethanol, including up to about 30% ethanol, including up to about 20% ethanol, including up to about 10% ethanol, including up to about 3% ethanol, including up to about 0.75% ethanol. In one exemplary embodiment, the liquid is tap water, however, the liquid can be distilled water, deionized water, tap water, filtered water, saline, water with acidic properties, and water with basic properties. In some exemplary embodiments the formulation includes water, alcohol, and one or more additional additives. In some exemplary embodiments, the additive is a stabilizer. Use of a stabilizer enables the activated wipe to retain its antimicrobial benefits for a longer period than would otherwise exist with formulations that do not have a stabilizer. An exemplary stabilizer is an alcohol, such as, for example, ethanol, or isopropyl alcohol. Other exemplary additives that may help stabilize the activated fluid may be included quaternary ammonium group, such as, for example, benzalkonium chloride. Additives that are considered preservatives, such as, for example methylparaben, propylparaben, phenoxyethanol and the like may be used to stabilize the activated compound in some embodiments. In some embodiments, glycol, such as, for example, caprylyl glycol, propylene glycol and the like may be used as a stabilizer. In some embodiments, nonvolatile glycol ether, such as, for example, ethylene glycol n-hexyl ether, ethylene glycol n-butyl ether and the like may be used as a stabilizer. In some embodiments, combinations of one or more of the above exemplary additives may be used to stabilize the activated fluid.

In some exemplary embodiments, the properties of the liquid may be altered prior to activation by plasma or indirect plasma to increase or decrease concentration of species, radicals and the like. For example, the pH of the liquid may be adjusted to be acidic or basic. The pH may be adjusted, for example, by adding acid to the water prior to activation. Furthermore, the pH level may be lowered through the activation process. In one embodiment, the pH level of the activated water is 3.0, or about 3.0. In another embodiment the pH is between 2.0 and 3.5, or about 2.0 and about 3.5. In another embodiment the pH is between 1.5 and 4.0, or about 1.5 and about 4.0. Still, in another embodiment the pH is less than 3.5, or less than about 3.5, and in another embodiment the pH is less than 3.0, or less than about 3.0.

The liquid can be mixed with additives to improve the antimicrobial efficacy against virus, bacteria, fungi and organic soil load (like blood, bodily fluids). Non-limiting examples of additives that can be added to the liquid include alcohol (e.g., ethanol, isopropyl alcohol), hydrogen peroxide, nitrite (e.g. sodium nitrite), bio active oil (e.g., limonene, coconut oil, grape seed oil, olive oil, thyme oil, carvacrol, cinnamaldehyde), acid (e.g., acetic acid, citric acid, nitrous acid, hydrochloric acid), enzyme (e.g., superoxide dismutase, nitrate reductase); quaternary ammonium group (e.g., benzalkonium chloride, didecyldimethylammonium chloride), preservatives (e.g., methylparaben, propylparaben, phenoxyethanol), glycol (e.g., caprylyl glycol, propylene glycol), nonvolatile glycol ether (e.g., ethylene glycol n-hexyl ether, ethylene glycol n-butyl ether), and any combinations thereof.

In addition, other additives may be used to optimize generation or increase performance and/or increase stability. These additives may include, for example, but not be limited to, chelators to reduce metal degradation; surfactants to improve penetration of the solution, to reduce the impact of organic load and/or buffers used to adjust the pH, and alcohol, such as ethanol to increase stability. In addition, in some embodiments corrosion inhibitors may be added, such as, for example, inorganic sulfates, and inorganic phosphates. In some embodiments, a zeolite buffering system may be used. In some embodiments, one or more of these additives are added prior to activation of the water.

Further, additives may be added before or after the liquid is activated to increase efficacy or stabilization of the resulting solution. Other additives that may be used depending on the desired results include, for example, alcohol, silver salts (e.g., silver nitrate or silver chloride, or colloidal silver); zinc salts (e.g. zinc chloride, zinc lactate, or zinc oxide); copper salts (e.g. copper sulphate); suspensions containing metal nanoparticles; chlorhexidine; anionic, cationic, nonionic and/or amphoteric surfactants; emulsifiers; hydrotropes; glycerol; chelating agents; alcohols; quaternary ammonium compounds, acids (organic or inorganic); bases; or surface tension decreasing agents.

In some exemplary embodiments, such as for example, where the application involves the disinfection of bacterial spores, the liquid used to moisten the wipe can include, but not be limited to, one or more of alcohol (e.g. ethanol, isopropyl alcohol); quaternary ammonium group (e.g., benzalkonium chloride); preservatives (e.g., methylparaben, propylparaben, phenoxyethanol); glycol (e.g., caprylyl glycol, propylene glycol); nonvolatile glycol ether (e.g., ethylene glycol n-hexyl ether, ethylene glycol n-butyl ether); or combinations thereof.

The surface may be any surface, such as, for example, a table, a bed, etc. made of polymer, metal, rubber, glass, silicone, fabric material or the like. The surface may be a hard surface or a soft surface, such as, for example, linens, curtains and the like. In addition, the surface may be tissue or skin.

The non-thermal plasma can be formed from any type of direct or indirect non-thermal plasma generator, such as a plasma jet, dielectric barrier discharge (DBD), DBD plasma jet, gliding arc, gliding spark, corona discharge, non-thermal arc discharge, pulsed spark discharge, hollow cathode discharge, micro-discharge, glow discharge, and the like. The voltage waveform generated by the plasma power supply can be DC, pulsed DC, pulsed AC, AC sinusoidal, RF, microwave and the like. The plasma can be driven by ambient air. The plasma can also be driven by feeding different gases. Non-limiting examples of feeding gas that may be used include noble gases (e.g., helium, argon), molecular gasses (e.g., oxygen, nitrogen), gas carrying evaporated liquids, or combination thereof.

In addition, the properties of the activated fluid may be adjusted during the activation process itself by altering the gas that is ionized at the electrode. For example, the gas that is ionized may be normal air, $N_2$, $O_2$, He, Ar, Xe, Kr, combinations thereof at various ratios, or the like. In some embodiments, one or more inert gases are used in the plasma generating process. In some embodiments, one or more noble gases are used in the plasma generating process, and in some embodiments, combinations of noble and other gases are used in the plasma generating process.

The amount of liquid in the pre-moistened sheet may vary with different embodiments. Any amount of liquid that when activated may effectively clean, disinfect, and sanitize a surface contaminated with bacteria, viruses, spores, fungi, or other contaminants, may be used. In one exemplary embodiment the amount of liquid in the pre-moistened sheet is in the range of 5-50 µL/cm$^2$, in another the amount of liquid is between 5-25 µL/cm$^2$, and in yet another embodiment the amount of liquid is between 9-17 µL/cm$^2$, Other operational variables may be modified in various embodiments of the method and system. Non-limiting examples of some variables that may vary among different embodiments include the thickness of wipe, the concentration of the liquid, the duration of time the wipe is exposed to plasma, the intensity of the plasma, the duration of time utilized for wiping down the surface, the duration of time the liquid from the wipe is allowed to remaining on the surface, and the duration of time between generating the plasma-activated wipe and utilizing the wipe on a surface.

Figure 4:
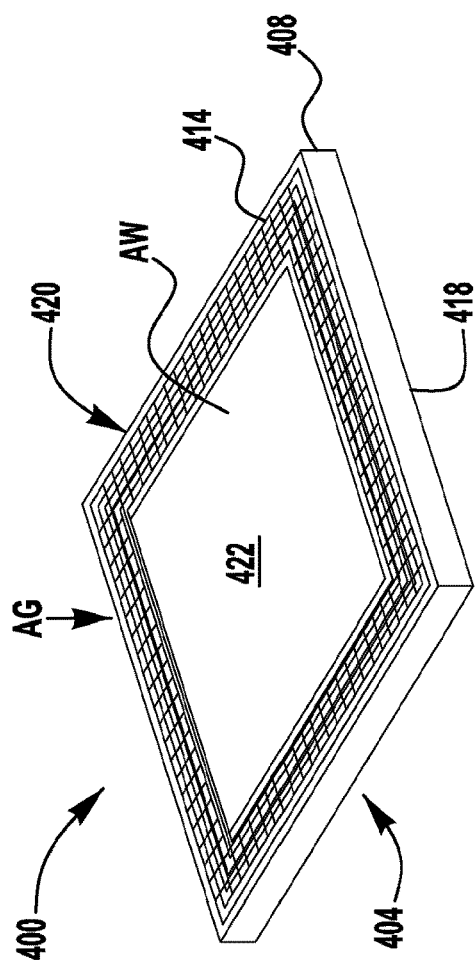
FIG. 4 illustrates an exemplary embodiment of a system for generating antimicrobial wipes by the method of FIG. 3.
Figure 5:
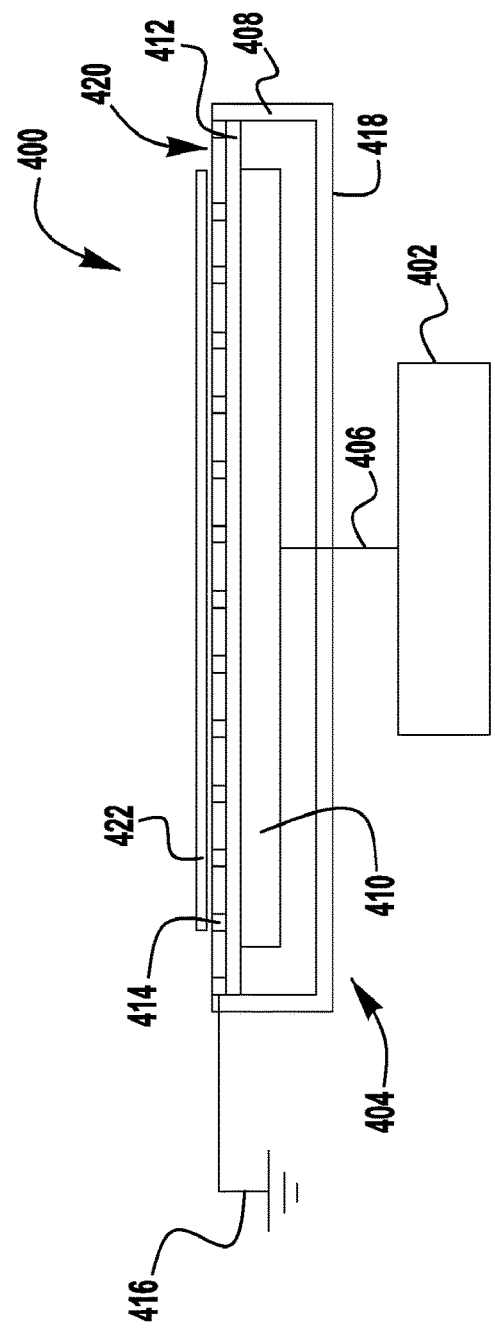
FIG. 5 is an illustration of the system of FIG. 4.

FIGS. 4 and 5 illustrate an exemplary embodiment of a system 400 for generating an antimicrobial wipe by the method of FIG. 3. The system 400 may be configured in a variety of ways. In the illustrated embodiment, the system 400 includes a high voltage power source 402. The high voltage power source 402 may be a high frequency AC power source, an RF power source, a microwave power source, a pulsed DC power source, a pulsed AC power source or any suitable power source.

The system includes an indirect DBD plasma generator 404 that is electrically coupled to the high voltage power source 402. The indirect DBD plasma generator 404 may be electrically coupled to the high voltage power source 402 by any suitable means, such as for example, by a cable 406. The indirect DBD plasma generator 404 includes a housing 408 that supports a high voltage electrode 410, a dielectric barrier 412, and a filter 414, such as a conductive mesh or conductive perforated sheet, as is known in the art, which is grounded by a grounding conductor 416. The dielectric barrier 412 is positioned between the high voltage electrode 410 and the filter 414. The housing 408 may be shaped and sized in a variety of ways. In the illustrated embodiment, the housing 408 is generally arranged as a box-shaped, platform-like configuration including a bottom face 418 designed to support the system 400 on a flat surface such as a table top, counter top, desk or the like. The filter 414 can be arranged generally parallel to the bottom face 418 of the housing 408 and can define at least a portion of an activating surface 420 of the plasma generator 404. In the illustrated embodiment, the filter 414 and dielectric barrier 412 have a surface area AG that approximately equal to or greater than the surface area AW of a pre-moistened wipe 420 to be activated by the system. In other embodiments, however, the surface area AG of the system may be less than the surface area AW of the pre-moistened wipe 422.

In some embodiments, the system 400 includes an interface (not shown) to activate the system, such as turning on the plasma. The interface can be configured in a variety of ways. For example, in some embodiments, the interface can be a button, switch, remote control, or other interface that can be operated by a user. In some embodiments, the system 400 can include one or more sensors to detect one or more wipe conditions, such as for example, pH, saturation, activation level and one or more controllers that can automatically turn the plasma ON or OFF or adjust other variables based on sensed condition.

In operation, the system 400 can activate the liquid in the wipe 422. In particular, with the plasma generator 404 supported on a surface, a user may place a wipe 422 onto the filter 414 and turn the plasma generator ON. When the high voltage electrode 410 is energized, plasma forms above the dielectric barrier 412, and the filter 414 (if the filter is made of a conductive material and grounded) prevents charged ions and electrons from passing through and contacting the wipe 422. Thus, only neutral species pass through and activate the liquid in the wipe 422. The amount of time that the wipe 422 is activated by (or in contact with) the plasma is referred to as the activation time Ta. As discussed above, the activation time Ta may vary in different embodiments of the system.

Once the desired activation time Ta has elapsed, the wipe 422 may be used to wipe down a contaminated surface. The amount of time the wipe 422 is effective at cleaning, disinfecting, and sanitizing a contaminated surface can vary based on a number of factors, such as the activation time, the amount of activated liquid in the wipe, the intensity of the plasma, the type of liquid, the pH of the liquid, selected additives or stabilizers in the liquid, the amount of contamination and other factors. Thus, the amount of time the wipe 422 is effective may vary in different embodiments of the system.

The system 400 may include one or more timers (not shown) to automatically turn ON and OFF the plasma generators and/or provide one or more signals (e.g. audible, visual, etc.) to the user regarding when the wipe is ready for use and when the wipe needs to be discarded. In some embodiments, the activated wipe may change colors to indicate the wipe needs to be discarded. Furthermore, the system 400 may include one or more sensors for sensing an operational parameter, such as a condition of the wipe, and automatically turn on and off the plasma generators and provide one or more signals (e.g. audible, visual, etc.). Blocks diagrams of some exemplary embodiments of timer and sensor features are discussed in detail below. Although some exemplary embodiments disclose use of a filter, the filter does not have to be used and the wipe is activated by direct plasma.

Figure 6:
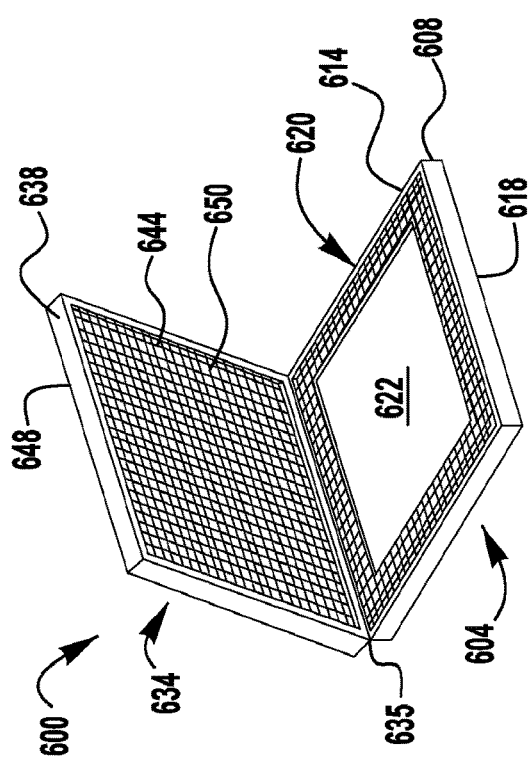
FIG. 6 illustrates an exemplary embodiment of a system for generating antimicrobial wipes by the method of FIG. 3.
Figure 7:
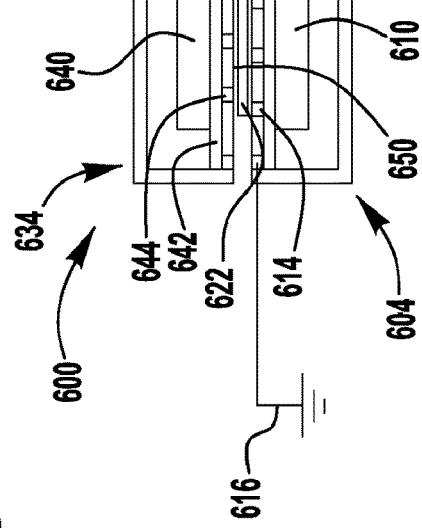
FIG. 7 is an illustration of the system of FIG. 6.

FIGS. 6 and 7 illustrate an exemplary embodiment of a system 600 for generating an antimicrobial wipe by the method of FIG. 3. The system 600 is similar to the system 400 of FIGS. 4 and 5 in that the system 600 includes a high voltage power source 602 electrically coupled to a first indirect DBD plasma generator 604 by any suitable means, such as for example, by a cable 606. The indirect DBD plasma generator 604 includes a housing 608 that supports a high voltage electrode 610, a dielectric barrier 612, and a filter 614 that is grounded by a grounding conductor 616. The dielectric barrier 612 is positioned between the high voltage electrode 610 and the filter 614. The housing 608 is generally arranged as a box-shaped, platform-like configuration including a bottom face 618 designed to support the system 600 flat surface such as a table top, counter top, desk or the like. The configuration of the housing 608, however, may vary in different embodiments. The filter 614 (if used) can be arranged generally parallel to the bottom face 618 of the housing 608 and can define at least a portion of an upper surface 620 of the first plasma generator 604.

The system 600, however, differs from the system 400 in that the system 600 includes a second plasma generator 634. The second plasma generator 634 is designed to face the first plasma generator 604 such that a pre-moistened wipe 622 can be sandwiched between the first and second plasma generators 604, 634. Thus, the first and second plasma generators 604, 634 may form a parallel plate plasma generating arrangement. The second plasma generator 634 may be separate from the first plasma generator 604 or may be movably connected to the first plasma generator. The second plasma generator 634 may be movably connected to the first plasma generator 604 in any suitable manner, such as for example, by a hinged connection 635 as shown in FIG. 6.

The second plasma generator 634 may be similar to the first plasma generator 604. For example, the second plasma generator 634 can be electrically coupled to the high voltage power source 602 or a separate high voltage power source (not shown). The second plasma generator 634 can be connected to a high voltage power source by any suitable means, such as for example, by a cable 636. The second plasma generator 634 includes a housing 638 that supports a high voltage electrode 640, a dielectric barrier 642, and a grounded filter 644. The dielectric barrier 642 is positioned between the high voltage electrode 640 and the filter 644. The housing 638 is generally arranged in a box-shaped configuration including a top face 648. The filter 644 can be arranged generally parallel to the top face 648 of the housing 638 and can define at least a portion of a lower surface 650 of the second plasma generator 634.

In operation, the system 600 can activate the liquid in the pre-moistened wipe 622. In particular, with the first plasma generator 604 supported on a surface, a user may place the wipe 622 onto the filter 614 and then lower the second plasma generator 634 such that the wipe 622 is sandwiched between the first and second plasma generators 604, 634. When the high voltage electrodes 610, 640 are energized, plasma forms above the dielectric barrier 612 of the first plasma generator 604 and below the dielectric barrier 642 of the second plasma generator 634. As with the system 400 of FIG. 4, the activation time Ta of the wipe 622 and the amount of time the wipe 622 is effective at cleaning, disinfecting, and sanitizing a contaminated surface can vary based may vary in different embodiments of the system. Furthermore, similar to the system 400, the system 600 may include sensor and timer features that automatically turn ON and OFF the plasma generators and/or provide one or more signals (e.g. audible, visual, etc.) to the user regarding when the wipe is ready for use and when the wipe needs to be discarded.

Figure 9:
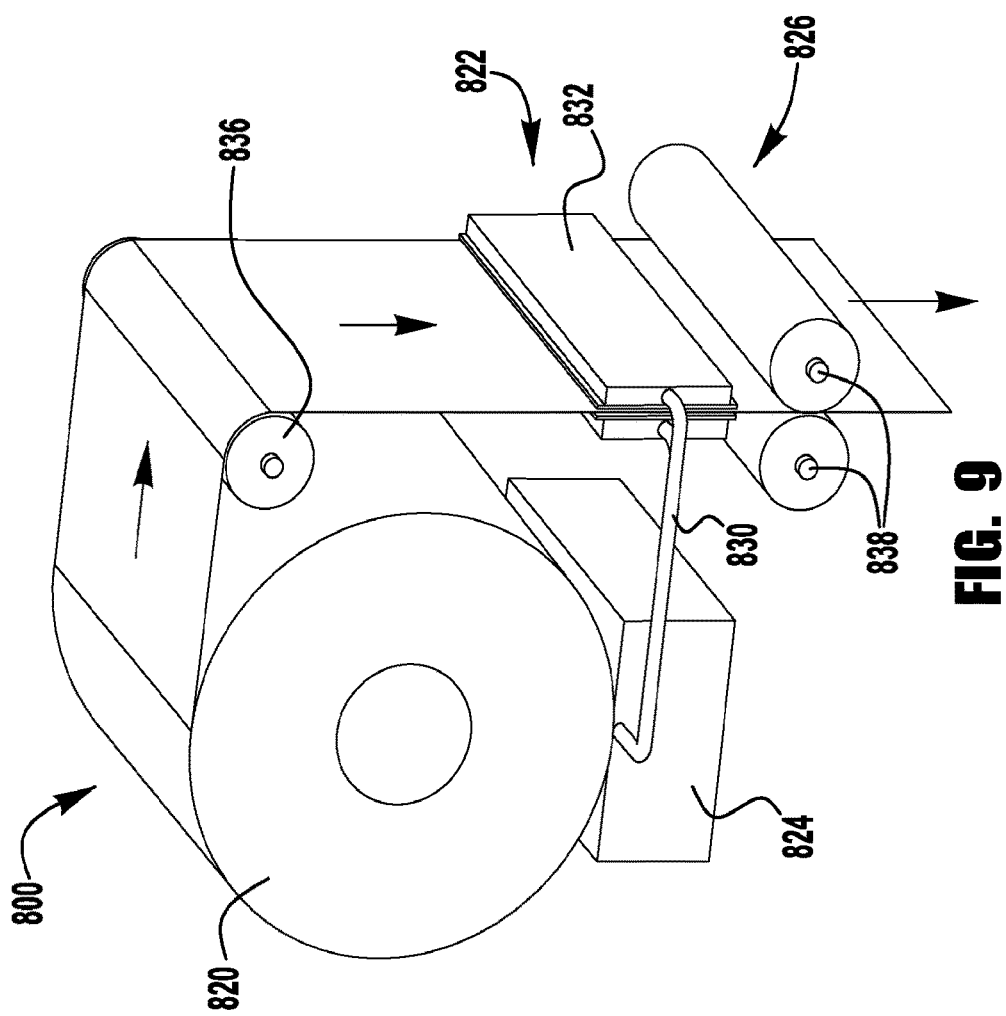
FIG. 9 illustrates an exemplary embodiment of the system of FIG. 8 with a housing removed.
Figure 8:
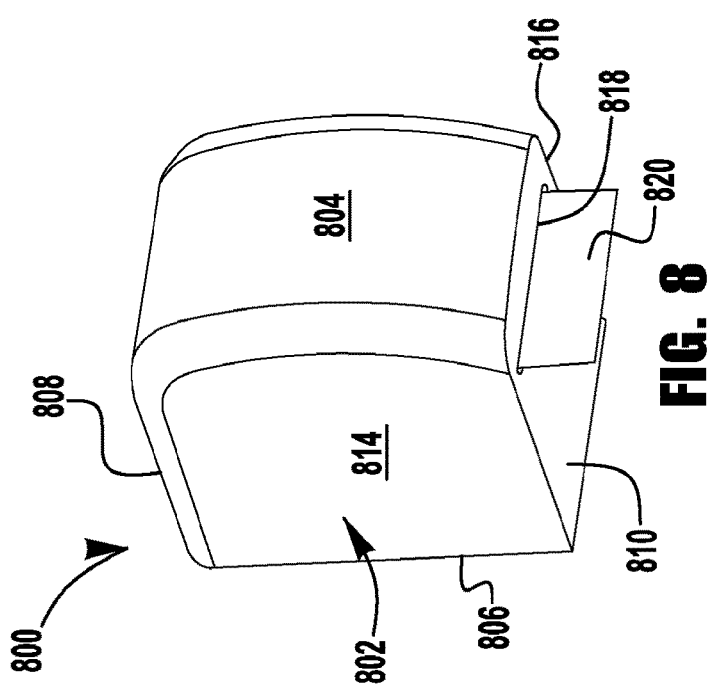
FIG. 8 illustrates an exemplary embodiment of a housing for a system for generating antimicrobial wipes by the method of FIG. 3.

FIGS. 8 and 9 illustrate another exemplary embodiment of a system 800 for generating an antimicrobial wipe by the method of FIG. 3. The system 800 may be configured in a variety of ways. In the illustrated embodiment, the system 800 is configured as an automatic wipe dispenser. In particular, the system 800 includes a housing 802. The size and shape of the housing may vary in different embodiments. In the illustrated embodiment, the housing 802 is generally box-shaped having a front side 804, a rear side 806 spaced apart from and generally parallel to the front side, a top side 808, a bottom side 810 spaced apart from and generally parallel to the top side 808, a left side 814, and a right side 816, spaced apart from and generally parallel to the left side. The housing includes an opening 818 for dispensing wipes 820. In the illustrated embodiment, the opening 818 is a slot arranged on the bottom side 810 of the housing 802. In other embodiments, however, the opening 818 may be shaped and positioned on the housing in any suitable manner.

The system 800 further includes, disposed within the housing 802, a supply of pre-moistened wipes 820, one or more plasma generators 822, a plasma power supply 824, and a feed system 826 capable of moving one or more wipes from the supply of wipes, to the plasma generators and out of the opening 818. The supply of pre-moistened wipes 820 may be configured in a variety of ways. In the illustrated embodiment, the supply of wipes 820 are arranged as a roll of wipes that is rotatably mounted in the housing 802.

The one or more plasma generators 822 may be configured in a variety of ways. In the illustrated embodiment the one or more plasma generators 822 includes a parallel plate plasma generator 822 that is electrically coupled to the plasma power supply 824 by one or more cables 830. Parallel plate plasma generator 832 may be configured and operate similar to any of the plasma generators described herein, such as for example, the plasma generators 604, 634 of the system 600 of FIGS. 6 and 7. The plasma power supply 824 may be any suitable power supply, such as for example the high voltage power source 402 of FIG. 4.

The feed system 826 may be configured in a variety of ways. Any system capable of moving one or more wipes from the supply of wipes, to the plasma generators and out of the opening 818 may be used. For example, the feed system 826 may be a conventional feed system for a manual or powered paper towel dispenser. In one embodiment, the feed system 826 includes one or more roller systems, each including one or more rollers. In the illustrated embodiment of FIG. 9, the feed system 826 includes a first roller 836 positioned between the supply of wipes 820 and the parallel plate plasma generator 830. The feed system 826 also includes a pair of pinch rollers 838 positioned between the parallel plate plasma generator 830 and the opening 818. In the exemplary embodiment, the pinch rollers 838 are powered, as is known in the art, to feed the wipes in a machine direction, shown by the arrow in FIG. 9. The feed system 826 may be powered by any suitable means, such as for example, battery power, line power, or manually.

In some embodiments, the system 800 includes an interface (not shown) to activate the system, such as turning on the plasma and/or the feed system 826. The interface can be configured in a variety of ways. For example, in some embodiments, the interface can be a button, switch, remote control, or other interface that can be engaged by a user. In some embodiments, the system 800 can include one or more sensors to detect one or more conditions, such as for example, pH or saturation of the wipe, activation status of the wipe, feed system speed, amount of wipes remaining, or other conditions. In some embodiments, the system 800 can include one or more controllers that can turn the plasma ON or OFF, adjust feed speed other variables based on sensed condition. Similar to the system 400, the system 800 may include sensor and timer features that automatically turn ON and OFF the plasma generators and/or provide one or more signals (e.g. audible, visual, etc.) to the user regarding when the wipe is ready for use and when the wipe needs to be discarded. In some embodiments, the interface may be a sensor for sensing a hand or object below system 800.

For the illustrated exemplary embodiment, in operation, the system 800 is activated by the user. Once activated, the feed system 826 draws a continuous sheet of connected wipes from the roll of pre-moistened wipes 820 in the machine directions (shown by the arrows in FIG. 9). The sheet of wipes is drawn between parallel plates of the plasma generator 822. The plasma generator 822 is turned ON, either at the same time as the system is activated or separately. The sheet of wipes may pause between the parallel plates for a duration of time, such as for example, the activation time Ta. Alternatively, the sheet may move past the parallel plates of the plasma generator at a speed slow enough to expose the sheet to plasma for activation time Ta. In some embodiments multiple plasma generators may be used.

Once a wipe in the continuous sheet of connected pre-moistened wipes have been exposed to the plasma from the one or more plasma generators for the activation time Ta, the feed system advances the wipe out of the opening 818 so that the user may separate the wipe from the continuous sheet of wipes 820 and use the wipe to clean, disinfect, and sanitize a surface.

Figure 10:
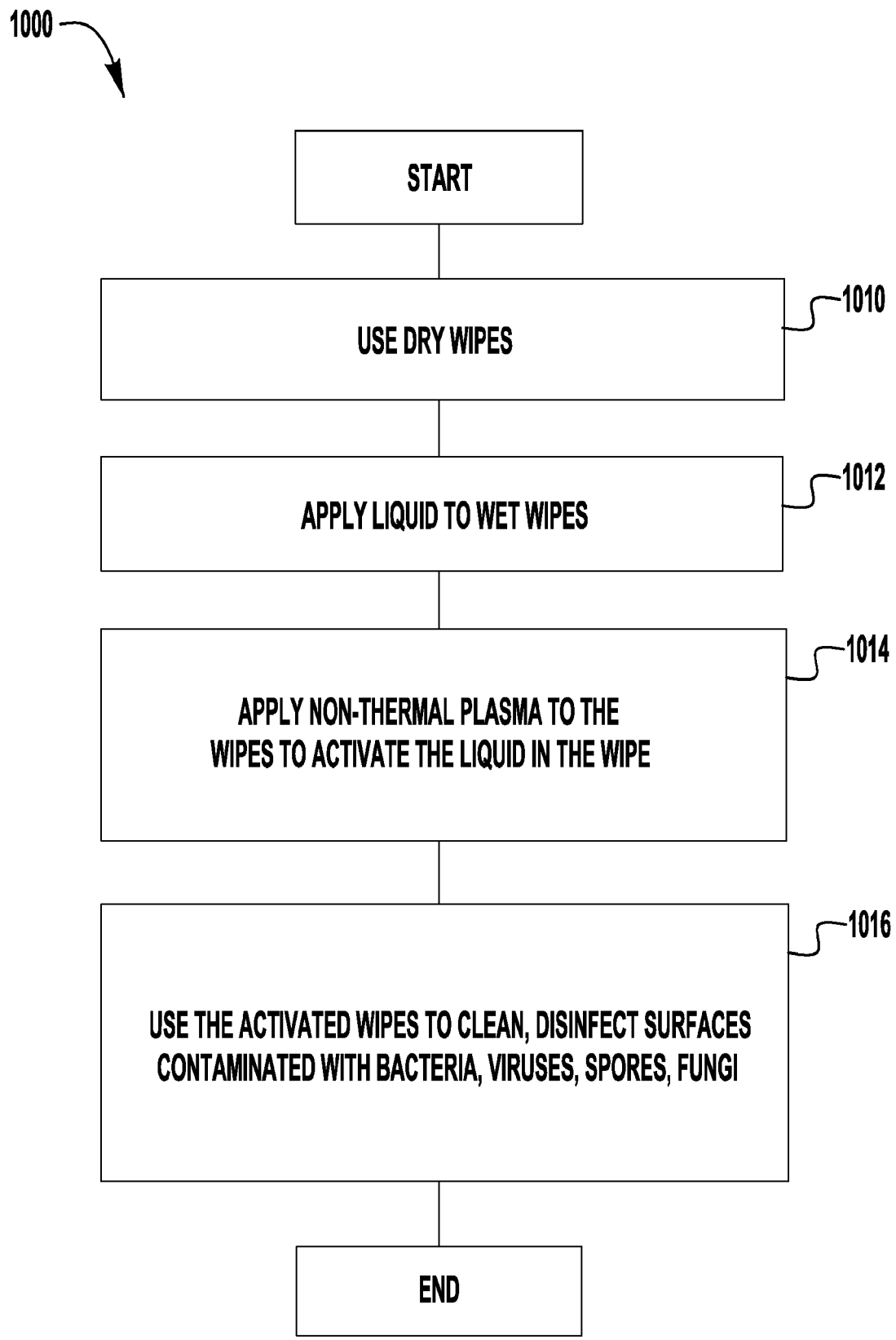
FIG. 10 illustrates an exemplary method for generating antimicrobial wipes.

FIG. 10 illustrates another exemplary methodology 1000 of generating an antimicrobial wipe that can be used to clean and disinfect a surface contaminated with bacteria, viruses, spores, fungi, or combinations thereof. The methodology 1000 is similar to the methodology 300 of FIG. 3 except that instead of using pre-moistened wipes, the method 1000 uses dry wipes and moistens the dry wipes. In particular, the method 1000 includes, as shown in block 1010, providing one or more dry wipes and, as shown in block 1012, applying a liquid to wet the one or more dry wipes to form one or more moistened wipes. As shown in block 1014, non-thermal plasma can be applied to the one or more moistened wipes to activate the liquid in the one or more wipes. The activated one or more wipes can be used, as shown in block 1016, to wipe down a surface contaminated with bacteria, viruses, spores, fungi, or other contaminants in order to clean, disinfect, and sanitize the surface. In some exemplary embodiments, the liquid is periodically or continuously activated by plasma and is applied to dry wipes to moisten the dry wipes prior to the dispensing of the wipe.

Applying liquid to the wipes 1012 can be accomplished in a variety of ways. For example, liquid can be sprayed on the wipes, liquid could be fogged over the wipes, fountain coated over the wipes, the wipes can be dipped in a pool of liquid, the wipes can be exposed to a mist of liquid, or any other suitable manner of wetting the wipes. The amount of liquid and duration of time the liquid is applied to the wipes may vary in different embodiments.

Figure 11:
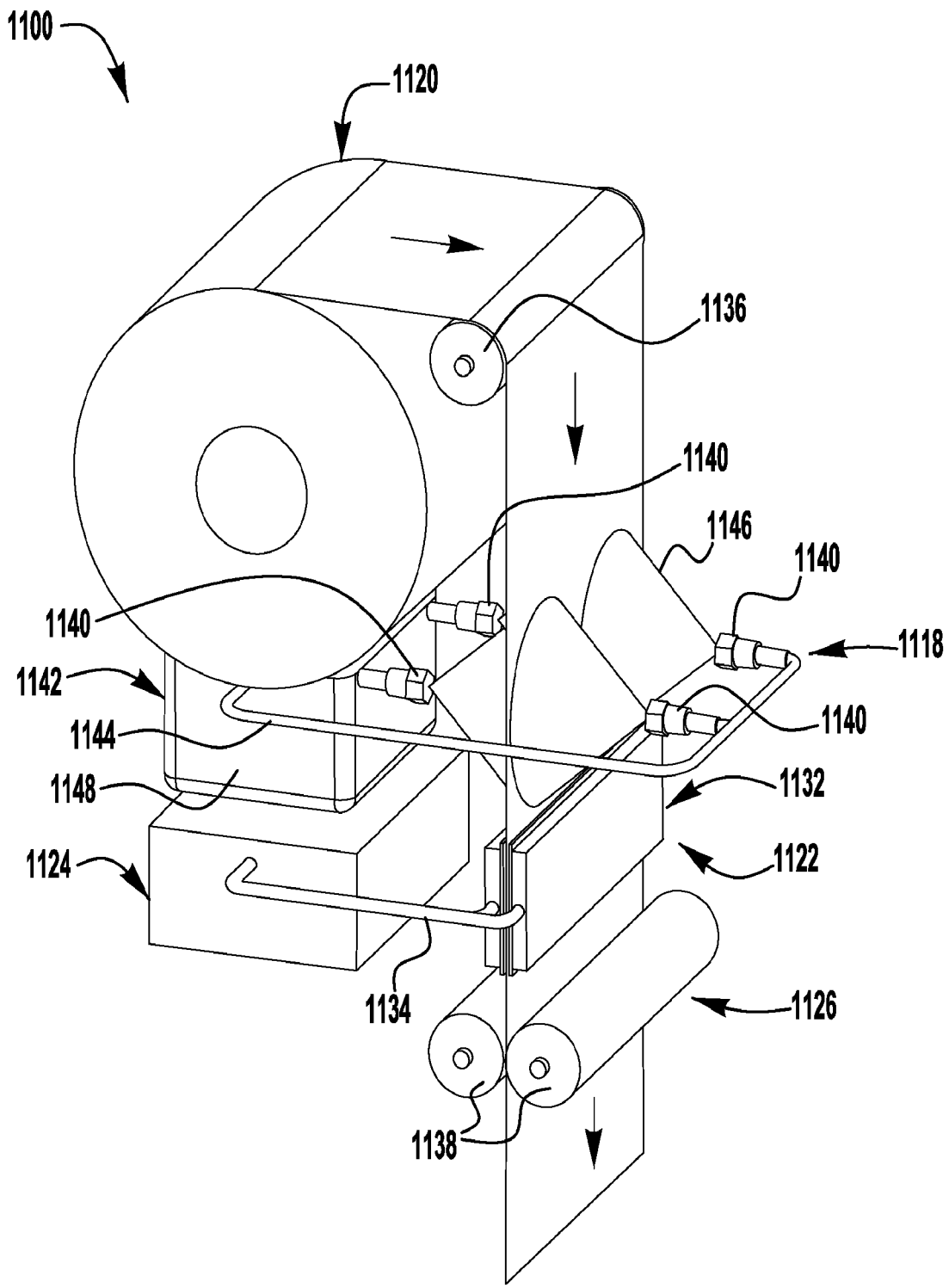
FIG. 11 illustrates an exemplary embodiment of a system for generating antimicrobial wipes by the method of FIG. 10.

FIG. 11 illustrates another exemplary embodiment of a system 1100 for generating an antimicrobial wipe. The system 1100 is similar to the system 800 of FIGS. 8 and 9 except the system 1100 includes a wipe wetting system 1118. The system 1100 includes, disposed within a housing (not shown), a supply of dry wipes 1120, the wipe wetting system 1118, one or more plasma generators 1122, a plasma power supply 1124, and a feed system 1126 capable of moving one or more wipes from the supply of wipes, to the wipe wetting system 1118, to the plasma generators 1122, and out of the housing (not shown). The supply of dry wipes 1120 may be configured in a variety of ways. In the illustrated embodiment, the supply of wipes 1120 are arranged as a roll of wipes that is rotatably mounted in the housing (not shown).

The wipe wetting system 1118 may be configured in a variety of ways. Any device capable of sufficiently wetting the wipes such that the liquid in the wipe can be activated by plasma to form an activated wipe capable of cleaning, disinfecting, and sanitizing a surface contaminated with bacteria, viruses, spores, fungi, or other contaminants may be used. In the illustrated embodiment, the wipe wetting system 1118 includes one or more of spray nozzles 1140 connected to a source of liquid 1142 by one or more fluid conduits 1144, such as for example, fluid hoses or pipes.

The one or more spray nozzles 1140 are configured to direct a spray or mist 1146 of liquid onto one or more wipes from the supply of wipes 1120. The one or more nozzles 1140 can be configured in a variety of ways. Any nozzle suitable for wetting the wipes may be used. In the illustrated embodiment, the one or more nozzles 1140 include four nozzles. In other embodiments, however, the one or more nozzles 1140 may be greater or less than four nozzles. The one or more nozzles can be arranged in a variety of ways. In the illustrated embodiment, the four nozzles are arranged in two pairs. A first pair is positioned to spray on a first side of the one or more wipes and the second pair is positioned to spray on the opposite side of the one or more wipes. Each of the nozzles is aimed generally perpendicular to the machine direction, shown by the arrow in FIG. 11. In other embodiments, however, the one or more nozzles may be in a different arrangement and may be aimed other than generally perpendicular to the machine direction.

The source of liquid 1142 may be configured in a variety of ways. In the illustrated exemplary embodiment, the source of liquid 1142 is disposed in a liquid container 1148 within the housing (not shown). In other embodiments, however, the source of liquid 1142 can be disposed in a liquid container external to the housing or supplied from another source. For example, the system 1100 may be connected to a water line to supply tap water to the dispenser.

The one or more plasma generators 1122 may be configured in a variety of ways, such as for example, as a parallel plate plasma generator 1132 that is electrically coupled to the plasma power supply 1124 by one or more cables 1134. The parallel plate plasma generator 1132 may be configured and operate similar to any of the plasma generators described above and the plasma power supply 1124 may be any suitable power supply, such as for example the high voltage power source 402 of FIG. 5.

The feed system 1126 may be configured in a variety of ways. For example, the feed system 1126 may be similar to the feed system 826 of FIG. 9. In the illustrated embodiment of FIG. 11, the feed system 1126 includes a first roller 1136 positioned between the supply of wipes 1120 and the wipe wetting system 1118 and a pair of powered pinch rollers 1138 positioned between the parallel plate plasma generator 1132 and an opening in the housing (not shown).

In some embodiments, the system 1100 includes an interface (not shown) to activate the system similar to the interface, one or more sensors to detect one or more conditions, such as for example, pH or saturation of the wipe, and one or more controllers that can turn the plasma ON or OFF, adjust feed speed, adjust the amount of liquid being used and duration of wetting, or other variables based one or more sensed conditions.

Figure 11A:
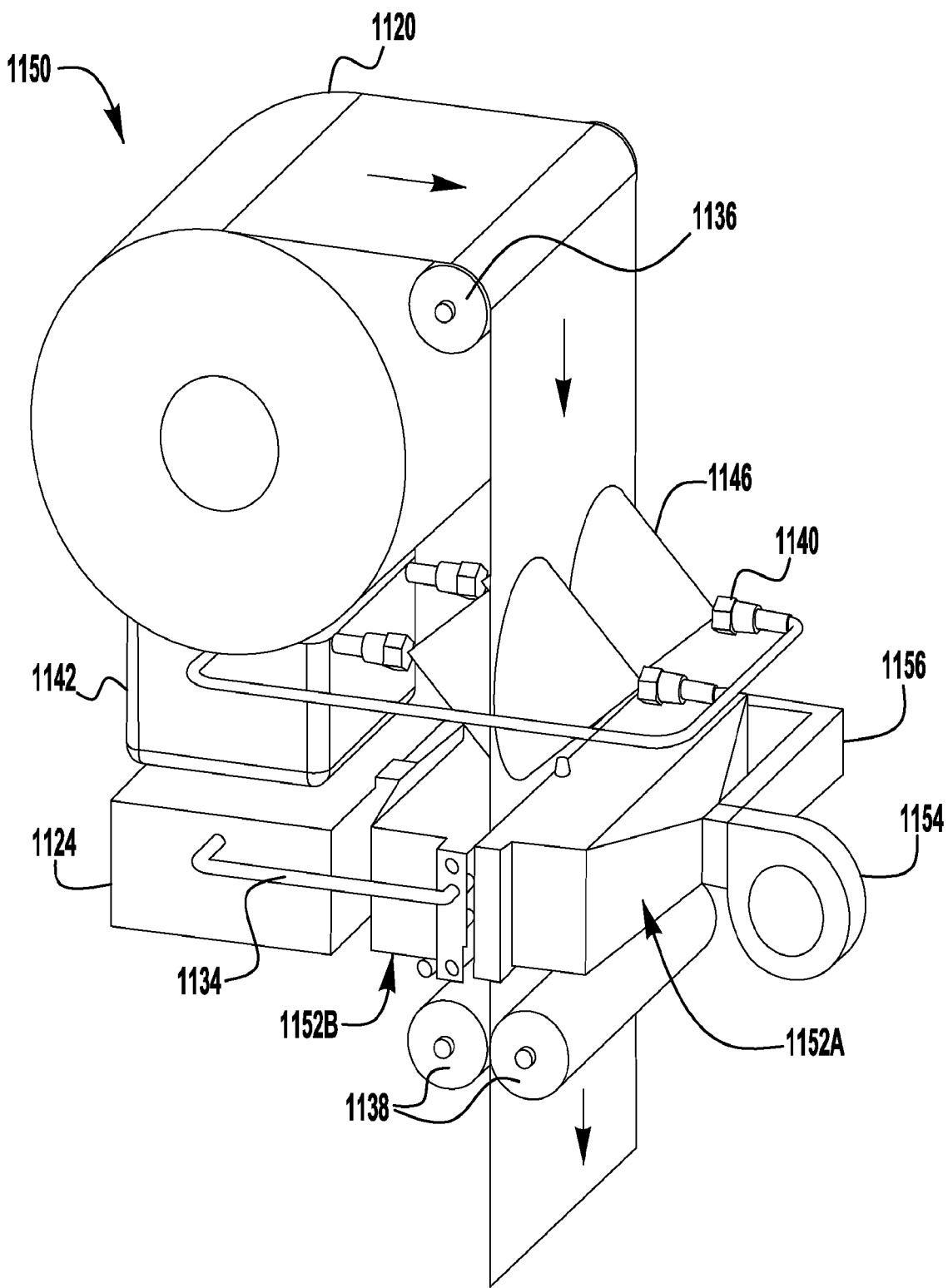
FIG. 11A illustrates another exemplary embodiment of a system for generating antimicrobial wipes by the method of FIG. 10.

FIG. 11A illustrates another exemplary embodiment of a system 1150 for generating an antimicrobial wipe. The exemplary system 1150 is similar to the system described above with respect to FIG. 11 and like numbered components are not be redescribed in this section. Rather than a parallel plate plasma generator, system 1150 includes a pair of forced air plasma generators 1152. Forced air plasma generators 1152 may be similar to the plasma generators described above, but include an air source to aid in causing the activated species to impregnate the wipe. The forced air plasma generators 1152A, B include an air source 1154, which may be, for example a fan. Air source 1154 is directly connected to the housing of plasma generator 1152A and duct work 1156 is provided to supply the forced air to the housing of plasma generator 1152B. During operation, the air source 1154 is powered and blows air through the housing of plasma generators 1152A, 1152B. The moistened wipes are activated. The forced air aids in the speed and depth of activation of the wipe by causing the plasma to contact the wipe surface, and in some embodiments penetrate into the wipe. In some embodiments, the forced air causes the wipe to be activated in less time. In some embodiments, the forced air causes fluid located deeper in the wipe to be activated. In some cases, the forced air causes a larger volume of liquid in the wipe to be activated.

Figure 12:
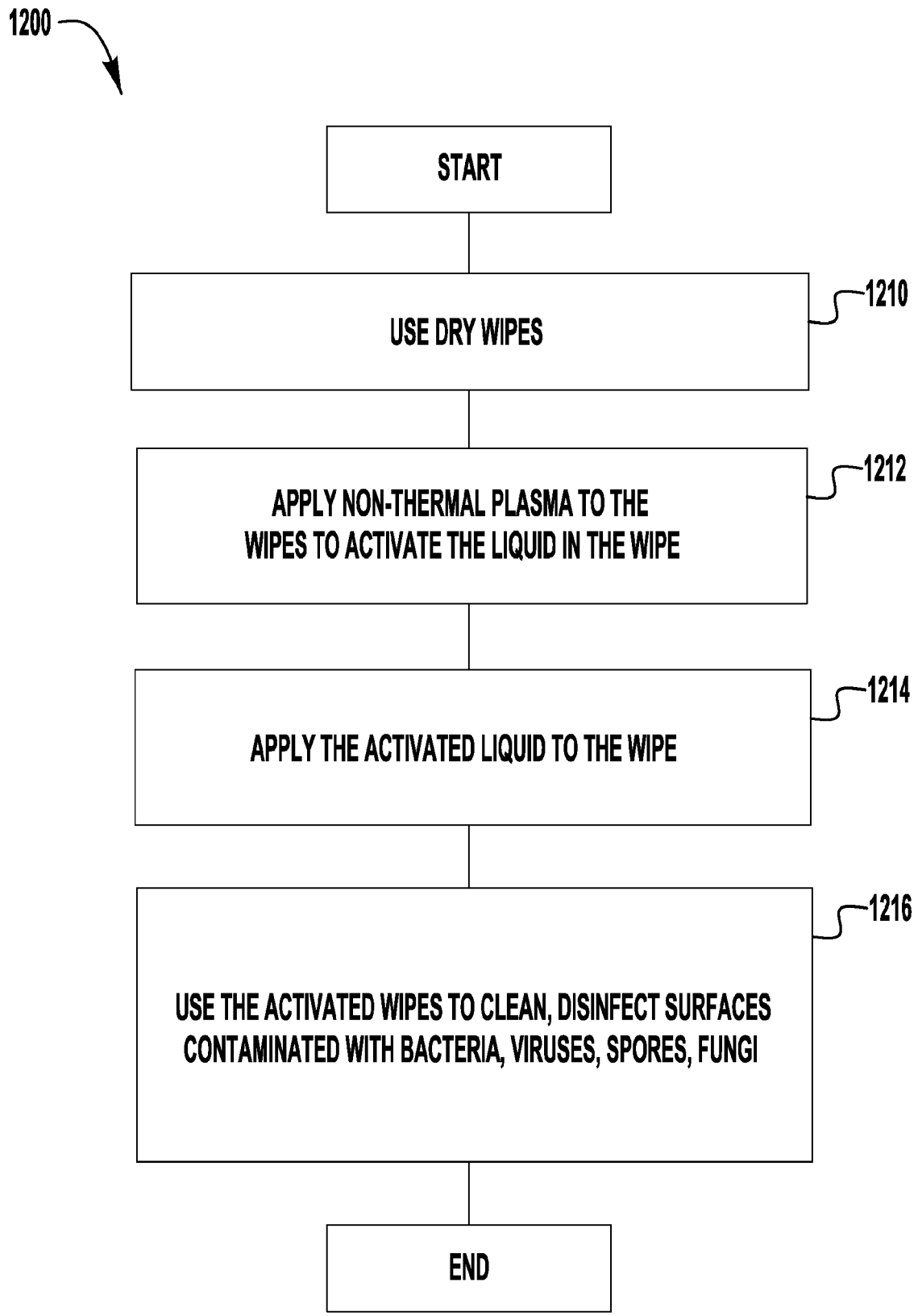
FIG. 12 illustrates an exemplary method for generating antimicrobial wipes.

FIG. 12 illustrates an exemplary methodology 1200 of generating an antimicrobial wipe that can be used to clean and disinfect a surface contaminated with bacteria, viruses, spores, fungi, or combinations thereof. The method 1200 is similar to the method 1000 of FIG. 10 except that instead of wetting the wipes and then applying plasma to the wetted wipes to activate the liquid, the method 1200 applies plasma to liquid to activate the liquid and then wets the wipe with the activated liquid. In particular, the method 1200 includes, as shown in block 1210, providing one or more dry wipes and, as shown in block 1212, applying non-thermal-plasma to a liquid to activate the liquid. As shown in block 1214, the activated liquid is then applied to the one or more wipes.

The activated one or more wipes can be used, as shown in block 1216, to wipe down a surface contaminated with bacteria, viruses, spores, fungi, or other contaminants in order to clean, disinfect, and sanitize the surface.

Applying non-thermal plasma to a liquid to activate the liquid 1212 can be accomplished in a variety of ways. Any method and device capable of suitably activating the liquid may be used. For example, in one exemplary embodiment, the step of applying non-thermal plasma to a liquid to activate the liquid 1212 can be accomplished using the device and method described in FIG. 2 above.

Figure 13:
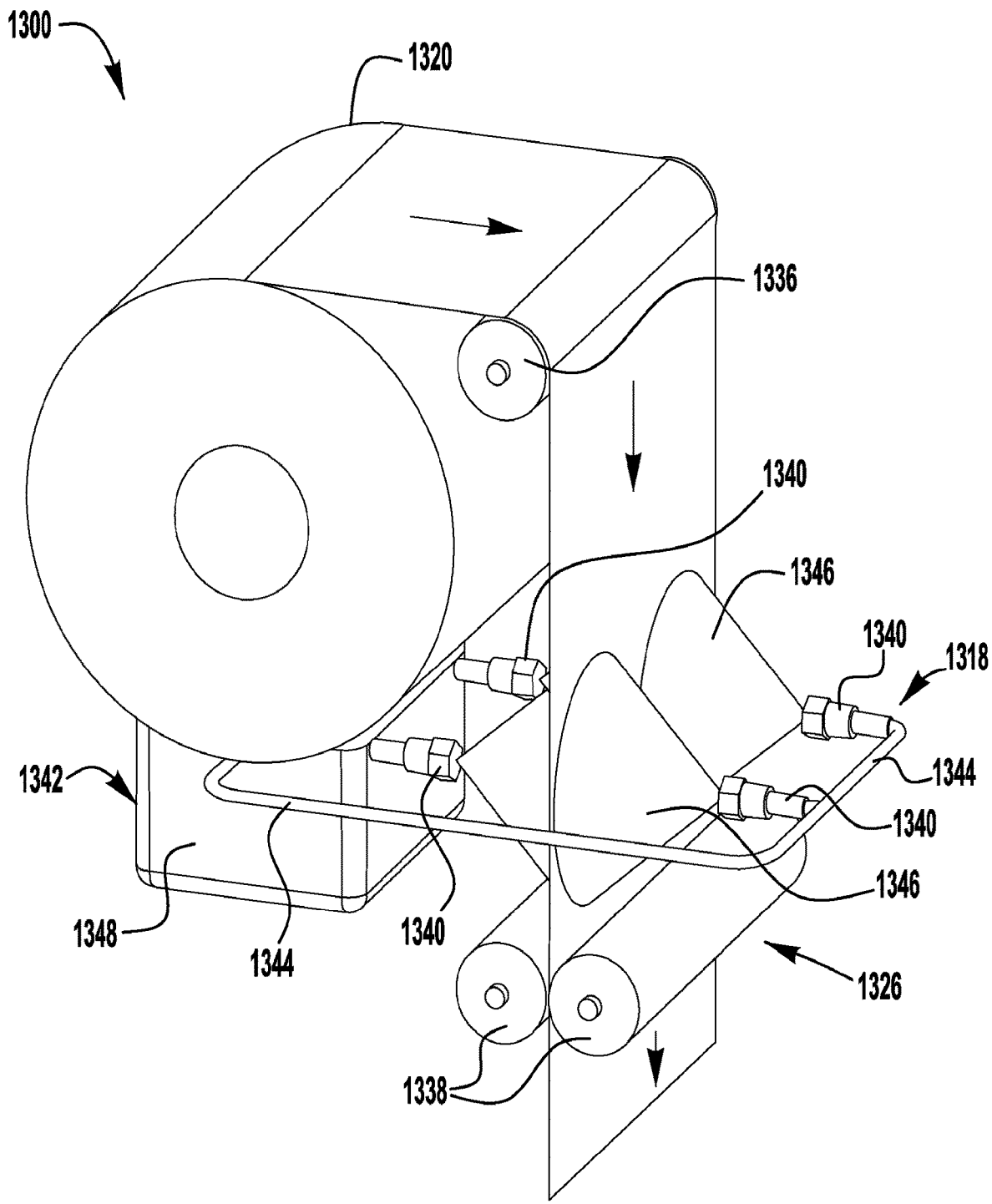
FIG. 13 illustrates an exemplary embodiment of a system for generating antimicrobial wipes by the method of FIG. 12.

FIG. 13 illustrates an exemplary embodiment of a system 1300 for generating an antimicrobial wipe by the method of FIG. 12. The system 1300 is similar to the system 1100 of FIG. 11 except that the system 1300 includes a source of plasma-activated liquid 1342. The source of plasma activated liquid may be made in any number of ways, such as, for example, a pump may be connected to liquid container 1348 to move the liquid contained therein through plasma created by a plasma generator (not shown) and recirculated back into liquid container 1348 thereby creating a constant supply of plasma activated liquid. The plasma activated liquid may be applied to the wipe by wetting system 1318. One or more plasma generators and a plasma power supply, however, may be external to and associated with the system 1300 in order to provide the source of plasma activated liquid 1342.

The system 1300 includes, disposed within a housing (not shown), a supply of dry wipes 1320, the wipe wetting system 1318 and a feed system 1326 capable of moving one or more wipes from the supply of wipes, to the wipe wetting system 1318, and out of the housing (not shown). The supply of dry wipes 1320 may be configured in a variety of ways. In the illustrated embodiment, the supply of dry wipes 1320 are arranged as a roll of wipes that is rotatably mounted in the housing (not shown).

The wipe wetting system 1318 may be configured in a variety of ways. Any device capable of sufficiently wetting the wipes with a plasma-activated liquid to form an activated wipe capable of cleaning, disinfecting, and sanitizing a surface contaminated with bacteria, viruses, spores, fungi, or other contaminants may be used. In the illustrated embodiment, the wipe wetting system 1318 includes one or more of spray nozzles 1340 connected to a source of plasma-activated liquid 1342 by one or more fluid conduits 1344, such as for example, fluid hoses or pipes.

The one or more spray nozzles 1340 are configured to direct a spray or mist 1346 of liquid onto one or more wipes from the supply of wipes 1320. In the illustrated embodiment, the one or more spray nozzles 1340 are four nozzles arranged in two pairs similar to the nozzles 1140 of the system 1100 of FIG. 11. The source of liquid 1342 may be configured in a variety of ways. In the illustrated exemplary embodiment, the source of liquid 1342 is disposed in a liquid container 1348 within the housing (not shown). In one embodiment, the liquid container 1348 may have a plasma generator (not shown) associated with container to plasma-activate the liquid in the container. In another embodiment, liquid may be plasma activated external to the system 1300 and transferred to the liquid container 1348.

The feed system 1326 may be configured in a variety of ways. For example, the feed system 1326 may be similar to the feed system 1126 of FIG. 11. In the illustrated embodiment of FIG. 13, the feed system 1326 includes a first roller 1336 positioned between the supply of wipes 1320 and the wipe wetting system 1318 and a pair of powered pinch rollers 1338 positioned between the wipe wetting system and an opening in the housing (not shown).

Similar to the system 1100 of FIG. 11, in some embodiments, the system 1300 includes an interface (not shown) to activate the system, one or more sensors to detect one or more conditions, such as for example, pH or saturation of the wipe, and one or more controllers that can turn the wipe wetting system ON/OFF, adjust feed speed, adjust the amount of liquid being used and duration of wetting, or other variables based on one or more sensed conditions.

Figure 14:
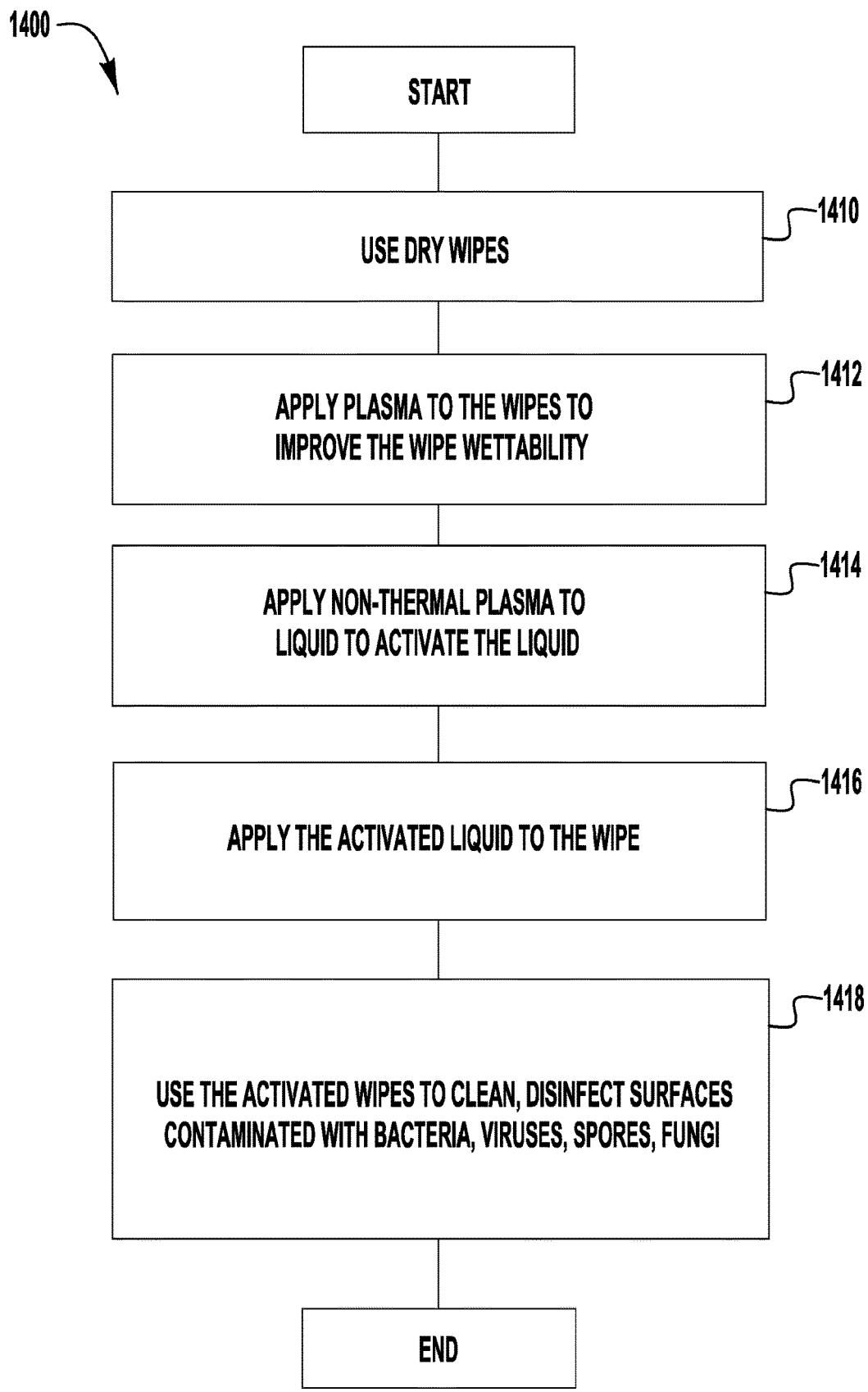
FIG. 14 illustrates an exemplary method for generating antimicrobial wipes.

FIG. 14 illustrates an exemplary method 1400 of generating an antimicrobial wipe that can be used to clean and disinfect a surface contaminated with bacteria, viruses, spores, fungi, or combinations thereof. The method 1400 is similar to the method 1200 of FIG. 12 except that plasma is applied to the dry wipes prior to wetting the wipes with plasma-activated liquid. In particular, the method 1400 includes, as shown in block 1410, providing one or more dry wipes and, as shown in block 1412, applying non-thermal-plasma to the wipes to improve or modify the wipe wettability of the wipe. As shown in block 1414, non-thermal plasma is also applied to a liquid to activate the liquid, then, as shown in block 1416, the activated liquid is applied to the one or more wipes. The activated one or more wipes can be used, as shown in block 1418, to wipe down a surface contaminated with bacteria, viruses, spores, fungi, or other contaminants in order to clean, disinfect, and sanitize the surface.

Applying non-thermal plasma to the dry wipes 1412 can be accomplished in a variety of ways. For example, non-thermal plasma may be applied to the dry wipes 1412 in the same manner as non-thermal plasma is applied to the wet wipes in any of the previously described methods, such as for example, method 300 of FIG. 3. Applying non-thermal plasma to a liquid to activate the liquid 1414 can be accomplished in a variety of ways. For example, non-thermal plasma may be applied to a liquid in the same manner as non-thermal plasma to a liquid in method 1200 of FIG. 12.

The methodologies disclosed herein may be modified, combined with one another, lengthened or shortened. Portions of methodologies may be combined or substituted with portions of other methodologies. For example, in another embodiment, the blocks 1414 and 1416 can be replaced by blocks 1012 and 1014 in FIG. 10 to create the activated wipes. In addition, steps from certain methodologies may be removed.

Figure 15:
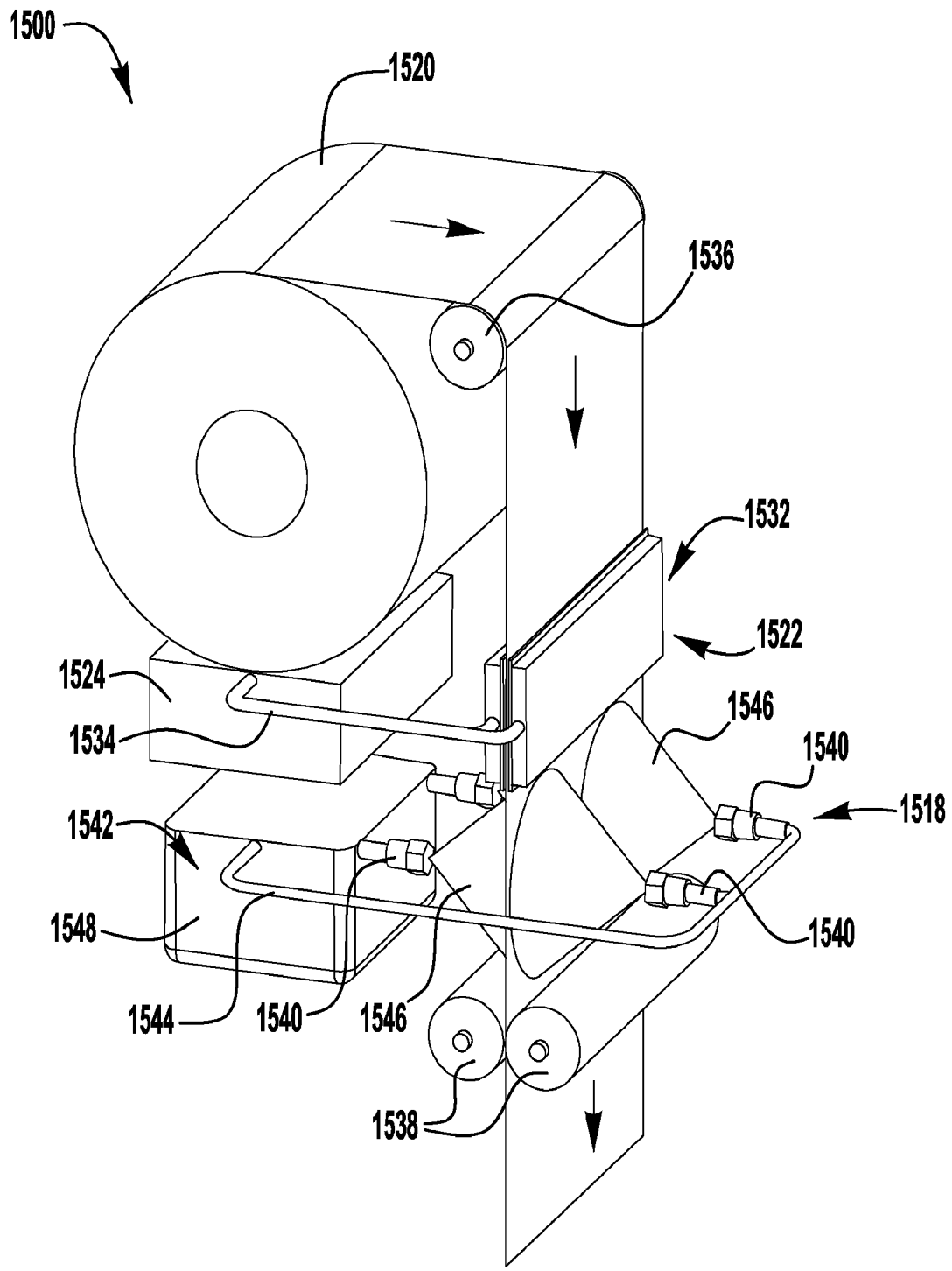
FIG. 15 illustrates an exemplary embodiment of a system for generating antimicrobial wipes by the method of FIG. 14.

FIG. 15 illustrates an exemplary embodiment of a system 1500 for generating an antimicrobial wipe by the method of FIG. 14. The system 1500 is similar to the system 1100 of FIG. 11 and the system 1300 of FIG. 13 except the system 1500 includes one or more plasma generators 1532 prior to a wipe wetting system 1546. In particular, the system 1500 includes, disposed within a housing (not shown), a supply of dry wipes 1520, one or more plasma generators 1522, a plasma power supply 1524, a wipe wetting system 1546, and a feed system 1538 capable of moving one or more wipes from the supply of wipes, to the plasma generators 1522, to the wipe wetting system 1518, and out of the housing (not shown). The supply of dry wipes 1520 may be configured in a variety of ways. In the illustrated embodiment, the supply of wipes 1520 are arranged as a roll of wipes that is rotatably mounted in the housing (not shown).

The wipe wetting system 1518 may be configured in a variety of ways. Any device capable of sufficiently wetting the wipes with a plasma-activated liquid to form an activated wipe capable of cleaning, disinfecting, and sanitizing a surface contaminated with bacteria, viruses, spores, fungi, or other contaminants may be used. In the illustrated embodiment, the wipe wetting system 1518 includes one or more of spray nozzles 1540 connected to a source of plasma-activated liquid 1542 (which may be activated intermittently or continuously as described herein or known in the art) by one or more fluid conduits 1544, such as for example, fluid hoses or pipes.

The one or more spray nozzles 1540 are configured to direct a plasma activated spray or mist 1546 of liquid onto one or more wipes from the supply of wipes 1520. The one or more nozzles 1540 can be configured in a variety of ways. Any nozzle suitable for wetting the wipes may be used. In the illustrated embodiment, the one or more nozzles 1534 are configured similar to the one or more nozzles of the wipe wetting system of 1318 of FIG. 13.

The source of plasma-activated liquid 1542 may be configured in a variety of ways. In the illustrated exemplary embodiment, the source of liquid 1542 is disposed in a liquid container 1548 within the housing (not shown). In one embodiment, the liquid container 1548 may have a plasma generator (not shown) associated with container to plasma-activate the liquid in the container. In another embodiment, liquid may be plasma-activated external to the system 1500 and transferred to the liquid container 1548.

The one or more plasma generators 1522 may be configured in a variety of ways, such as for example, as a parallel plate plasma generator 1532 that is electrically coupled to the plasma power supply 1524 by one or more cables 1534. The parallel plate plasma generator 1532 may be configured and operate similar to any of the plasma generators described above and the plasma power supply 1524 may be any suitable power supply, such as for example the high voltage power source 402 of FIG. 5.

The feed system 1538 may be configured in a variety of ways. For example, the feed system 1538 may be similarly configured and operate similar to any of the feed systems described above. In the illustrated embodiment of FIG. 15, the feed system 1538 includes a first roller 1536 positioned between the supply of wipes 1520 and the one or more plasma generators 1532 and a pair of powered pinch rollers 1538 positioned between wipe wetting system 1518 and an opening in the housing (not shown).

In some embodiments, the system 1500 includes an interface (not shown) to activate the system similar to the interface, one or more sensors to detect one or more conditions, such as for example, pH or saturation of the wipe, an activated level sufficient to kill or deactivate bacteria and/or spores, and one or more controllers that can turn the plasma ON or OFF, adjust feed speed, adjust the amount of liquid being used and duration of wetting, or other variables based one or more sensed conditions.

Figure 16:
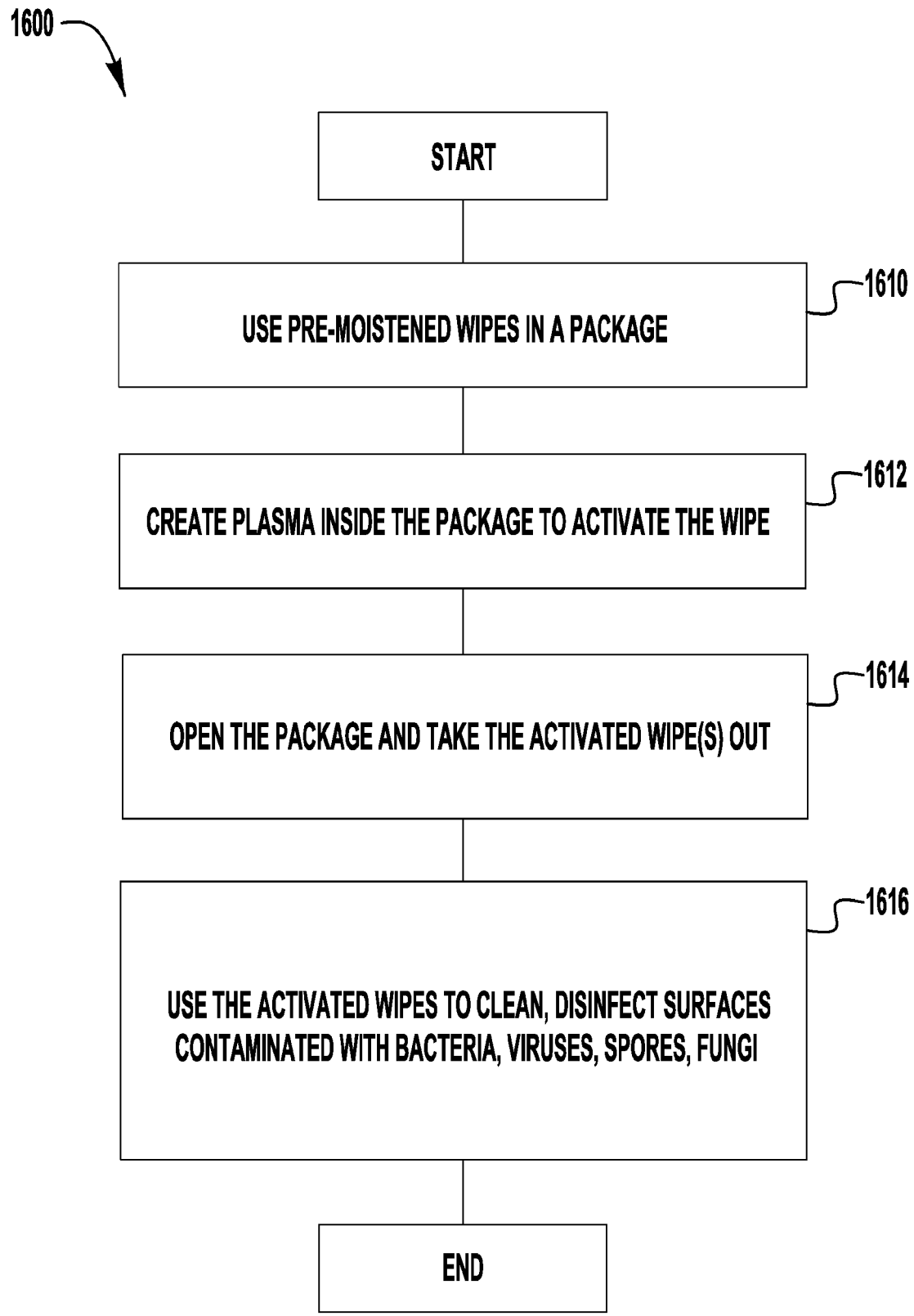
FIG. 16 illustrates an exemplary method for generating antimicrobial wipes.

FIG. 16 illustrates an exemplary methodology 1600 of generating an antimicrobial wipe that can be used to clean and disinfect a surface contaminated with bacteria, viruses, spores, fungi, or combinations thereof. The method 1600 includes, as shown in block 1610, providing one or more pre-moistened wipes in a package and, as shown in block 1612, creating plasma inside the package to activate the liquid in the one or more wipes. As shown in block 1614, the package of activated wipes can be opened and, the activated one or more wipes can be used, as shown in block 1616, to wipe down a surface contaminated with bacteria, viruses, spores, fungi, or other contaminants in order to clean, disinfect, and sanitize the surface.

Figure 17:
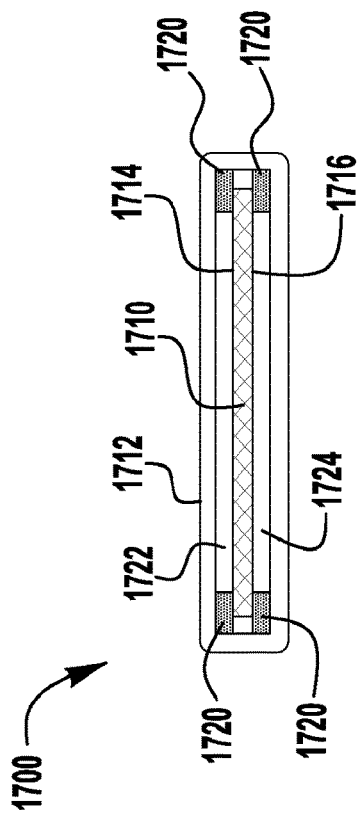
FIG. 17 illustrates an exemplary embodiment of a package of pre-moistened wipes for use by the method of FIG. 16.

FIG. 17 illustrates an exemplary embodiment of a package of one or more pre-moistened wipes 1700 designed to allow plasma to be created inside the package to activate the liquid in the wipes in the package. The package of one or more pre-moistened wipes 1700 may be formed and configured in a variety of ways. Any package that allows plasma to be created inside the package to activate the liquid in one or more wipes in the package may be used. In the exemplary embodiment of FIG. 17, the package 1700 includes one or more pre-moistened wipes 1710 positioned within a dielectric wrapper 1712 that at least partially surrounds the one or more wipes. The one or more wipes 1710 can take a variety of forms. For example, the one or more pre-moistened wipes can be formed the same as or similar to the one or more wipes of the method 300 of FIG. 3. FIG. 17 illustrates a single wipe 1710, but in other embodiments multiple wipes may be stacked together. The wipe 1710 includes a first face 1714 and a second face 1716 spaced apart from and parallel to the first face.

The dielectric wrapper 1712 can be formed in a variety of ways and from a variety of different materials. (Any wrapper 1712 that may at least partially surround the one or more wipes and allow plasma to be formed inside the package by an external plasma generator may be used). Non-limiting examples of materials that can be used for the dielectric package include, but are not limited to plastics, such as, for example, PE, Teflon, PP, rubber, silicone The package 1700 also includes one or more spacers 1720 positioned within the wrapper 1712 to create a first air gap 1722 between the wrapper and the first face 1714 of the wipe 1710 and a second air gap 1724 between the wrapper and the second face 1716 of the wipe. The one or more spacers 1720 can be configured in a variety of ways and made from a variety of different materials. Any number of spacers, shape of spacers, size of spacers, or material used in the spacers that can be used to create air gaps between the wipe and the wrapper and allow plasma to be generated in the air gaps may be used. For example, the one or more spacers may be shaped to follow the perimeter of the wipe 1710, thus the shape of each spacers 1720 may be the same or similar shape as the wipe. For example, in one embodiment, a rectangular shaped wipe may have a rectangular spacer engaging the first face 1714 around the perimeter of the wipe and another rectangular spacer engaging the second face 1716 around the perimeter of the wipe. Thus, the wipe 1710 is sandwiched between two spacers. In other embodiments, multiple spacers may be used on the first or second face to follow the perimeter of the wipe. In other embodiments, however, the one or more spacers need not be configured or arranged around the perimeter of the wipe. Furthermore, in some embodiments, each spacer may be configured to engage both faces of the wipe similar to a picture frame.

Figure 18:
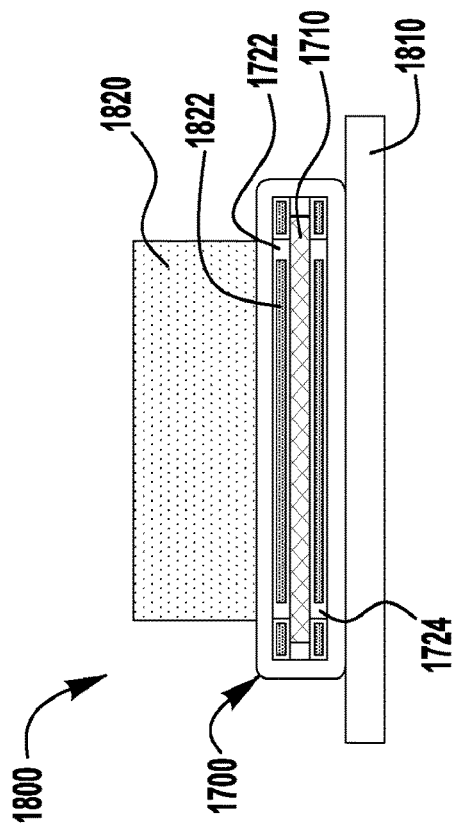
FIG. 18 illustrates an exemplary embodiment of a system for generating antimicrobial wipes by the method of FIG. 16 using the package of FIG. 17.

FIG. 18 illustrates an exemplary embodiment of an assembly 1800 for applying plasma to the package 1700 of FIG. 17. The assembly 1800 includes the package 1700 of FIG. 17 positioned on a grounded surface 1810 and one or more plasma generators 1820 positioned against or near the package opposite of the grounded surface. The one or more plasma generators 1820 can be configured in a variety of ways. For example the plasma generators 1820 can be any of the plasma generators described above, such as for example the plasma generator 400 of FIGS. 4 and 5. The ground surface 1810 can be any suitable grounded surface, such as for example, a grounded platform or table top.

In operation, when the package 1700 is sandwiched between the one or more plasma generators 1820 and the grounded surface 1810 and the one or more plasma generators are turned on, plasma 1822 can be formed in the air gaps 1722, 1724. The plasma 1822 may activate the liquid in the one or more pre-moistened wipes 1710 within the package 1700.

Figure 19:
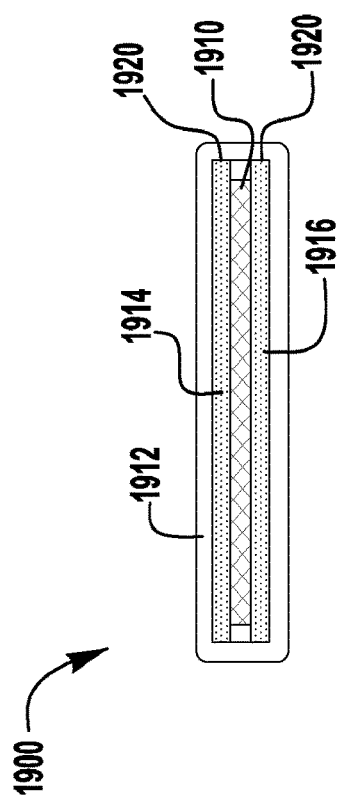
FIG. 19 illustrates an exemplary embodiment of a package of pre-moistened wipes for use by the method of FIG. 16.

FIG. 19 illustrates an exemplary embodiment of a package of one or more pre-moistened wipes 1900 designed to allow plasma to be created inside the package to activate the liquid in the wipes in the package. The package of one or more pre-moistened wipes 1900 may be formed and configured in a variety of ways. Any package that allows plasma to be created inside the package to activate the liquid in one or more wipes in the package may be used. In the exemplary embodiment of FIG. 19, the package 1900 includes one or more pre-moistened wipes 1910 positioned within a dielectric wrapper 1912 that at least partially surrounds the one or more wipes. The one or more wipes 1910 can take a variety of forms. For example, the one or more pre-moistened wipes 1910 can be formed the same as or similar to the one or more wipes 1710 of FIG. 3. FIG. 19 illustrates a single wipe 1910, but in other embodiments multiple wipes may be stacked together. The wipe 1910 includes a first face 1914 and a second face 1916 spaced apart from and parallel to the first face.

The dielectric wrapper 1912 can be formed in a variety of ways and from a variety of different materials. For example, the dielectric wrapper 1912 can be formed the same as or similar to the dielectric wrapper 1712 of FIG. 17.

The package 1900 also includes one or more dielectric hydrophobic porous elements 1920 positioned within the wrapper 1912. The one or more dielectric hydrophobic porous elements 1920 can be configured in a variety of ways and made from a variety of different materials. Any number of elements, shape of the elements, size of the elements, or dielectric hydrophobic porous materials used in the elements that can be positioned between the wipes and the wrapper and allow plasma to be generated between the elements and the wipes may be used. In the illustrated embodiment, the one or more dielectric hydrophobic porous elements 1920 is positioned between the first face 1914 of the wipe 1910 and the wrapper 1912 and another dielectric hydrophobic porous element 1920 positioned between the second face 1916 of the wipe 1910 and the wrapper 1912 such that the wipe 1910 is sandwiched between dielectric hydrophobic porous elements.

Figure 20:
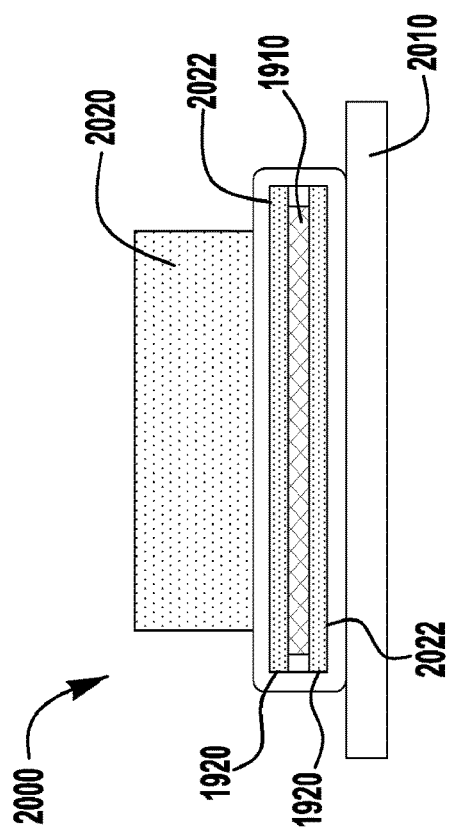
FIG. 20 illustrates an exemplary embodiment of a system for generating antimicrobial wipes by the method of FIG. 16 using the package of FIG. 19.

FIG. 20 illustrates an exemplary embodiment of an assembly 2000 for applying plasma to the package 1900 of FIG. 19. The assembly 2000 includes the package 1900 of FIG. 19 positioned on a grounded surface 2010 and one or more plasma generators 2020 positioned against or near the package opposite of the grounded surface. The one or more plasma generators 2020 can configured in a variety of ways. For example the plasma generators 2020 can be any of the plasma generators described above, such as for example the plasma generator 1820 of FIG. 18. The ground surface 2010 can be any suitable grounded surface, such as for example, a grounded platform or table top.

In operation, when the package 1900 is sandwiched between the one or more plasma generators 2020 and the grounded surface 2010 and the one or more plasma generators are turned on, plasma 2022 can be formed at the first face 1914 and the second face 1916 of the wipe 1910. The plasma 2022 may activate the liquid in the one or more pre-moistened wipes 1910 within the package 1900.

Figure 21:
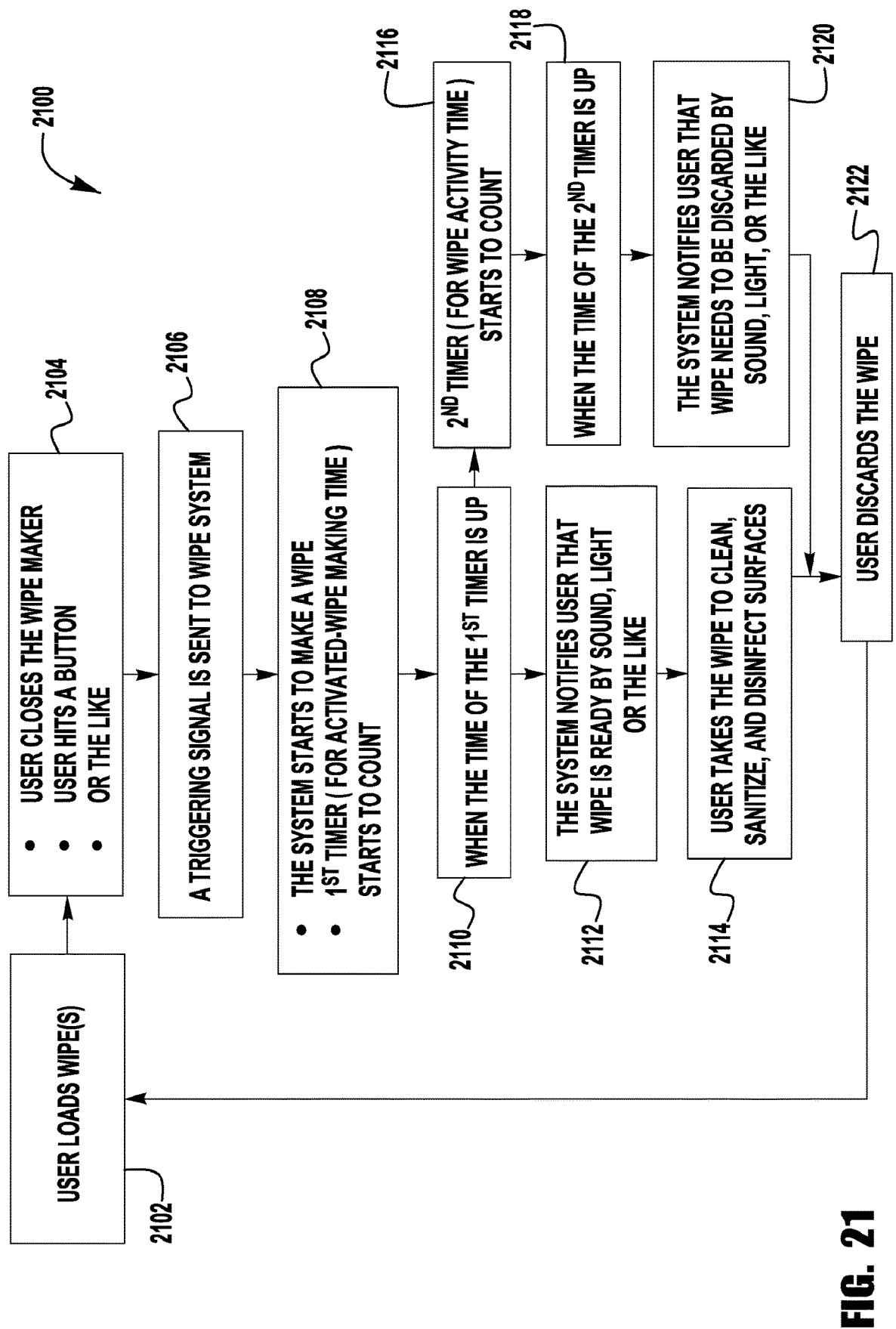
FIG. 21 illustrates a block diagram of an exemplary embodiment of timer feature for use with a system for generating antimicrobial wipes.

FIG. 21 illustrates a block diagram of an exemplary embodiment of a timer feature 2100 for a manually loaded system for generating an antimicrobial wipe, such as for example, the system 600 of FIGS. 6 and 7. The timer feature 2100 can be integrated into the system in a variety of ways. For example, the system may include timer IC, analog/digital convertor, microcontroller, voltage regulator, LEDs and buzzers. As shown in block 2102, a user manually loads a wipe into the system. The user, as shown in block 2104, then closes the system, if applicable, and activates the system. In some embodiments, closing the system may automatically activate the system. In other embodiments, the user may activate the system by turning on the system or otherwise providing power to the system. For example, the system may include an interface (not shown) such as a button, switch, remote control, or other interface that can be engaged by a user to activate the system.

Closing the system, engaging the interface or otherwise providing power to the system results in a triggering signal being sent to the system, as indicated in block 2106. In response to the triggering signal, the system starts the wipe generating process, as indicated in block 2108. The start of the wipe making process can vary depending on the system and method being used. The start of the wipe making process may include, for example, one or more of wetting a wipe, applying non-thermal plasma to a dry or pre-moistened wipe.

Coinciding with the start of the wipe making process, a first timer starts to count. The first timer provides a count indicating the duration of the wipe making process. When the first timer reaches a predetermined or user selected timer limit, as indicated in block 2110, such as for example, the time needed to generate an antimicrobial wipe, the system provides a signal to the user to indicate that the wipe is ready to be used, as indicated in block 2112. The signal can be any suitable signal, such as audible, visual, vibration, or other suitable signal or combinations thereof. Once the system notifies the user that the wipe is ready, the user may take the wipe from the system and use the wipe to wipe down a surface contaminated with bacteria, viruses, spores, fungi, or other contaminants in order to clean, disinfect, and sanitize the surface, as indicated by block 2114.

Coinciding with the first timer reaching the predetermined timer limit 2110, a second timer starts to count, as indicated in block 2116. The second timer provides a count indicating the duration that the wipe may be effective to clean, disinfect, and sanitize the surface. When the second timer reaches a predetermined or user selected timer limit, as indicated in block 2118, such as for example, the duration of time that the antimicrobial wipe is expected to still have a suitable efficacy, the system provides a signal to the user to indicate that the wipe should be discarded, as indicated in block 2120. After using the wipe to clean, disinfect, and sanitize the surface and/or after the second timer has reached the predetermined timer limit, the user may discard the wipe, as indicated by block 2122. If the user desires another wipe, the process can be restarted at block 2102 by loading another wipe into the system.

Figure 22:
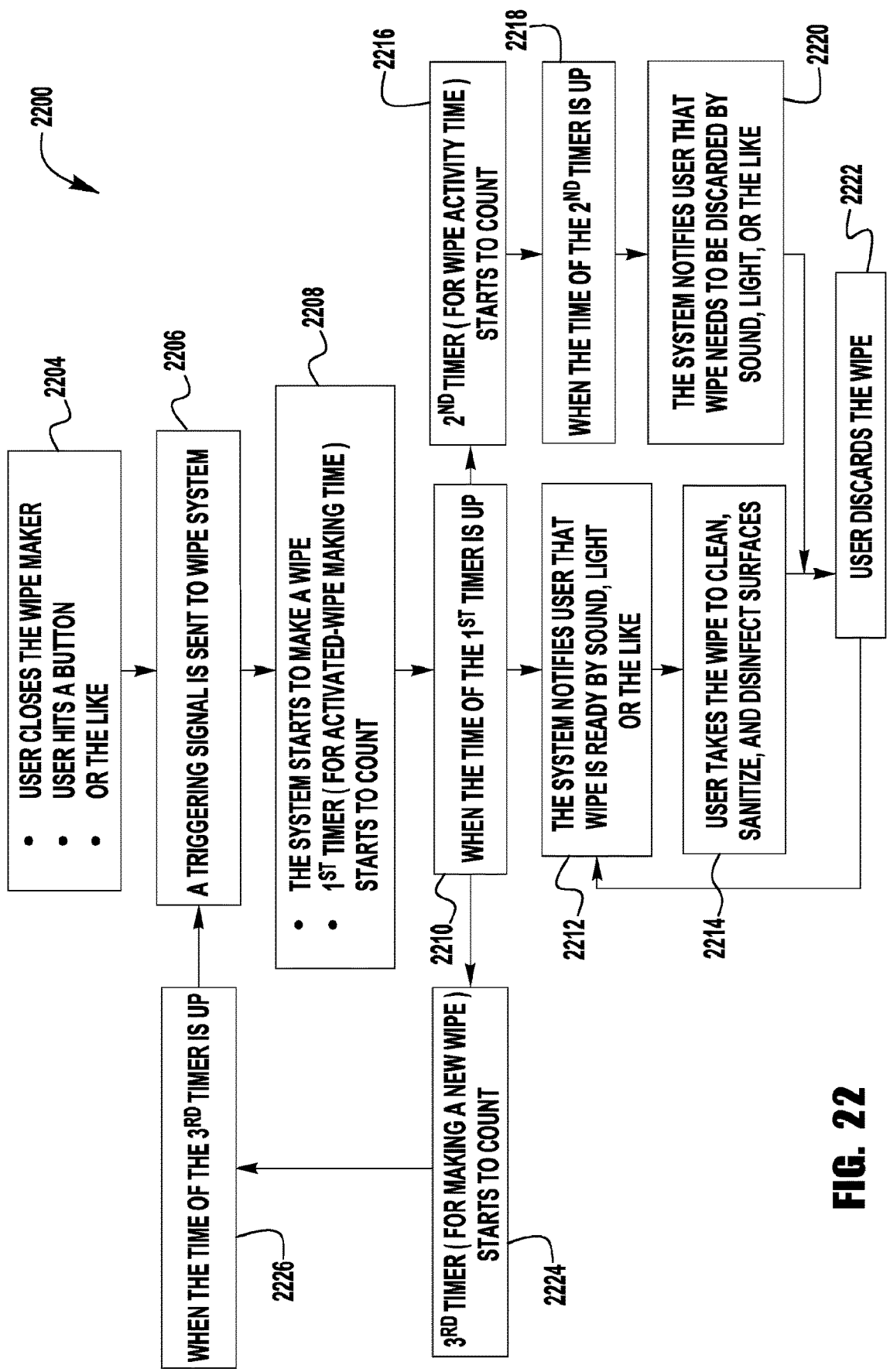
FIG. 22 illustrates a block diagram of an exemplary embodiment of timer feature for use with a system for generating antimicrobial wipes.

FIG. 22 illustrates a block diagram of an exemplary embodiment of a timer feature 2200 for an automatic system for generating an antimicrobial wipe, such as for example, the system 800 of FIG. 8. The timer feature 2200 can be integrated into the system in a variety of ways. To generate an antimicrobial wipe, with a supply of wipes loaded into the system, a user, as shown in block 2204, closes the system, if applicable, and activates the system. In some embodiments, closing the system may automatically activate the system. In other embodiments, the user may activate the system by turning on the system or otherwise providing power to the system. For example, the system may include an interface (not shown) such as a button, switch, remote control, motion sensor, heat sensor, or other interface that can be engaged by a user to activate the system.

Closing the system, engaging the interface or otherwise providing power to the system results in a triggering signal being sent to the system, as indicated in block 2206. In response to the triggering signal, the system starts the wipe generating process, as indicated in block 2208. The start of the wipe making process can vary depending on the system and method being used. The start of the wipe making process may include, for example, one or more of wetting a wipe, engaging a feed system, or applying non-thermal plasma to a dry or pre-moistened wipe.

Coinciding with the start of the wipe making process, a first timer starts to count. The first timer provides a count indicating the duration of the wipe making process. When the first timer reaches a predetermined or user selected timer limit, as indicated in block 2210, such as for example, the time needed to generate an antimicrobial wipe, the system provides a signal to the user to indicate that the wipe is ready to be used, as indicated in block 2212. The signal can be any suitable signal, such as audible, visual, vibration, or other suitable signal or combinations thereof. Once the system notifies the user that the wipe is ready, the user may take the wipe from the system and use the wipe to wipe down a surface contaminated with bacteria, viruses, spores, fungi, or other contaminants in order to clean, disinfect, and sanitize the surface, as indicated by block 2214.

Coinciding with the first timer reaching the timer limit 2110, a second timer starts to count, as indicated in block 2216. The second timer provides a count indicating the duration that the wipe may be effective to clean, disinfect, and sanitize the surface. When the second timer reaches a predetermined or user selected timer limit, as indicated in block 2218, such as for example, the duration of time that the antimicrobial wipe is expected to still have a suitable efficacy, the system provides a signal to the user to indicate that the wipe is should be discarded, as indicated in block 2220. After using the wipe to clean, disinfect, and sanitize the surface and/or after the second timer has reached the timer limit, the user may discard the wipe, as indicated by block 2222.

Further coinciding with the first timer reaching the timer limit 2210, an optional third timer may start to count, as indicated in block 2224. The third timer provides a count indicating the duration of time before the system begins to generate another antimicrobial wipe. When the third timer reaches a predetermined or user selected timer limit, as indicated in block 2226, such as for example, the desired duration of time before the wipe generating process begins again, a triggering signal is sent to the system, as indicated in block 2206, and the system starts the wipe generating process again.

Figure 23:
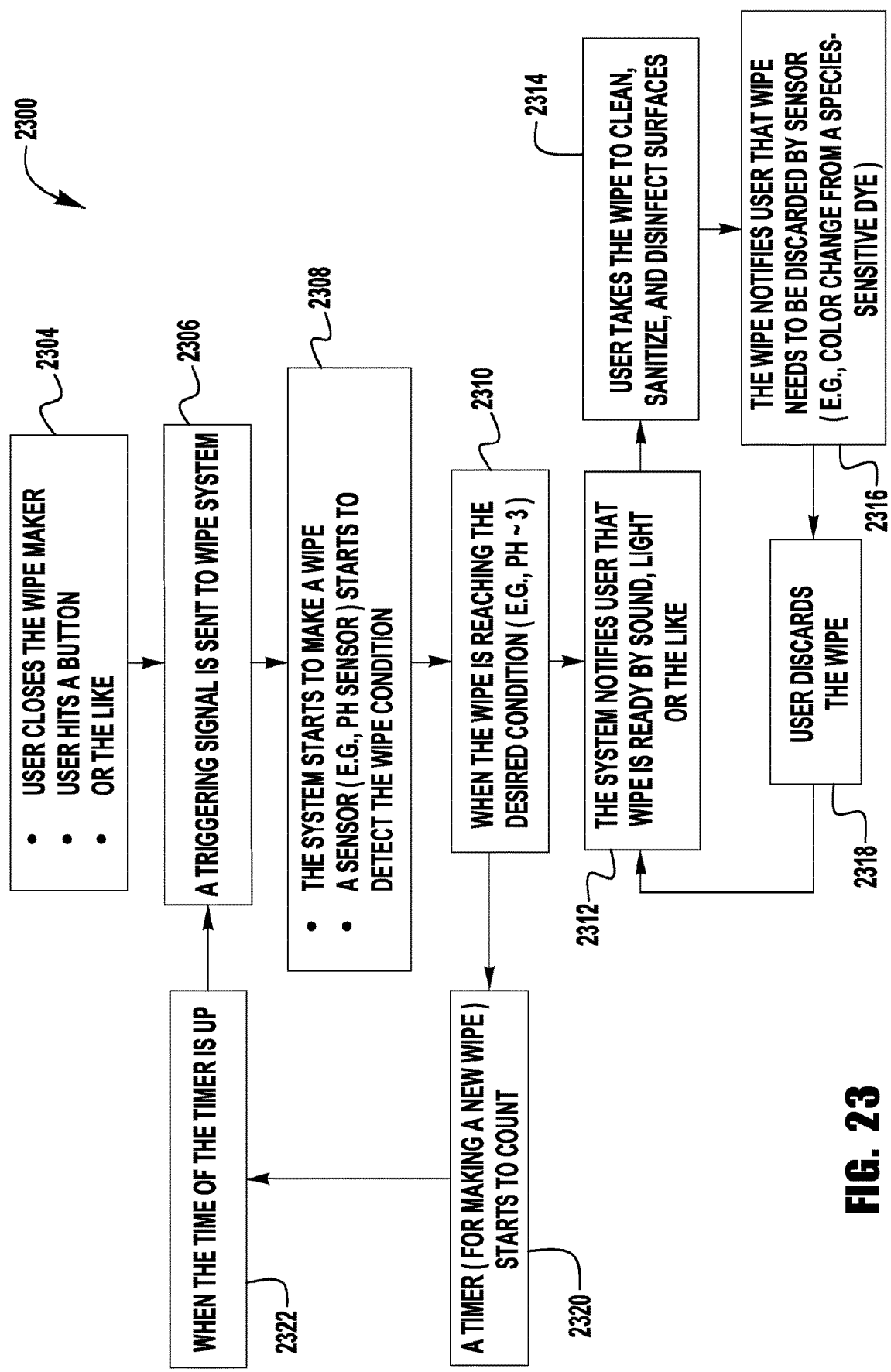
FIG. 23 illustrates a block diagram of an exemplary embodiment of sensor/timer feature for use with a system for generating antimicrobial wipes.

FIG. 23 illustrates a block diagram of an exemplary embodiment of a sensor/timer feature 2300 for an automatic system for generating an antimicrobial wipe, such as for example, the system 800 of FIG. 8. The sensor/timer feature 2300 can be integrated into the system in a variety of ways. The sensor feature can include one or more sensors that monitor and provide a feedback signal for a variety of parameters, such as for example, motion, presence of a hand or object, heat, sound or the like. In addition, the parameters may include timing, such as activating the system to ensure an activated wipe is always available for use.

Other sensors that may be included in the apparatuses described herein, include sensors that indicate a wipe is ready to use, such as, for example, pH sensors, activation concentration sensors or the like. In addition, sensors to determine that it is time to discard the wipe included bio-sensors may be used to determine organic load on the wipe to determine if it is above a threshold, color sensors to determine if the wipe had changed colors to indicate it should no longer be used and the like.

To generate an antimicrobial wipe, with a supply of wipes loaded into the system, a user, as shown in block 2304, closes the system, if applicable, and activates the system. In some embodiments, closing the system may automatically activate the system. In other embodiments, the user may activate the system by turning on the system or otherwise providing power to the system. For example, the system may include an interface (not shown) such as a button, switch, remote control, or other interface that can be engaged by a user to activate the system. Although some of the embodiments are described as requiring a user to activate the system, in some embodiments the presence of a user activates the system. In some embodiments, the system is activated on a timer. In some embodiments, the system is always activated.

Closing the system, engaging the interface or otherwise providing power to, or activating the system results in a triggering signal being sent to the system, as indicated in block 2306. In response to the triggering signal, the system starts the wipe generating process, as indicated in block 2308. The start of the wipe making process can vary depending on the system and method being used. The start of the wipe making process may include, for example, one or more of wetting a wipe, engaging a feed system, or applying non-thermal plasma to a dry or pre-moistened wipe.

Coinciding with the start of the wipe making process, at least one sensor monitors at least one operational parameter. In one embodiment, a sensor monitors a condition of the wipe during the wipe making process. For example, in one embodiment, a pH sensor monitors the pH level of the wipe, the antimicrobial efficacy of the wipe, a time of activation, a time since the wipe was activated, and the like. When the at least one operational parameter reaches a predetermined or user selected setting, as indicated in block 2310, such as for example, a desired pH level, the system provides a signal to the user to indicate that the wipe is ready to be used, as indicated in block 2312. The signal can be any suitable signal, such as audible, visual, vibration, ejecting a wipe or other suitable signal or combinations thereof. Once the system notifies the user that the wipe is ready, the user may take the wipe from the system and use the wipe to wipe down a surface contaminated with bacteria, viruses, spores, fungi, or other contaminants in order to clean, disinfect, and sanitize the surface, as indicated by block 2314.

In the illustrated embodiment of FIG. 23, the wipe can provide an indication when the wipe no longer has a suitable efficacy to clean, disinfect, and sanitize the surface. For example, the wipe may be treated with a species-sensitive dye that changes color in response to a change in pH of the wipe, the moisture level in the wipe, or other indicia of the efficacy of the wipe. In another example, the wipe may be treated with a bio-sensitive dye that changes color in response to the organic load or microbe load in the wipe. The change in color signals the user to discard the wipe, as indicated in block 2316. After using the wipe to clean, disinfect, and sanitize the surface and/or receiving an indication from the wipe, the user may discard the wipe, as indicated by block 2318.

In some embodiments, coinciding with the sensor detecting that the at least one operational parameter has reached a predetermined or user selected limit, a timer begins to count, as indicated in block 2320. The timer provides a count indicating the duration of time before the system begins to generate another antimicrobial wipe. When the timer reaches a predetermined or user selected timer limit, as indicated in block 2322, such as for example, the desired duration of time before the wipe generating process begins again, a triggering signal is sent to the system, as indicated in block 2306, and the system starts the wipe generating process again.

Experimental Results

Experimental results demonstrated the ability to kill or deactivate C. diff spores with the exemplary systems and methodologies described herein. The method to test the sporicidal efficacy of plasma activated wipes against C. diff spores is based on the SOP No. MB-32-00 published by US Environmental Protection Agency (EPA).

C. diff spores (ATCC 43598) were applied onto sterile glass Petri plates (150×20 mm). Five 10 µl of C. diff spores (~108 CFU/ml) in sterile water were added onto the inside bottom surface of each plate and left to dry for 30 min. The dry spores formed five visible spore spots on each plate. The contaminated surfaces were then wiped by selected wipes with or without plasma activation using corkscrew wiping pattern (the entire wiping process only takes 6±2 sec). After wiping, neutralizer was added to each plate and a sterile scraper was used to scrape the plate to recover the spores from the surface. The suspension was then transferred into test tubes. The test tubes were vortexed for 10 seconds. The neutralizer solution containing spores was diluted and plated on Brain Heart Infusion Agar supplemented with 0.1% Sodium Taurocholate (BHIT). Anaerobic incubation for 36-48 hr was then performed at 37° C., followed by the estimation of surviving colony forming units (CFU).

For all of the experiments, the apparatus described in FIGS. 4 and 5 with indirect dielectric barrier discharges (indirect DBD) was used to activate the liquid in the wipe.

In one experiment, a 3 cm×3 cm Rubbermaid HYGEN™ microfiber wipe was wetted with 160 µl of ethanol (EtOH) at different concentrations varying in the range of 0% (w/w) to 96% (w/w). The EtOH-wetted wipes were activated by the indirect DBD for 45 seconds. After plasma activation, the activated wipes were immediately used to wipe the spore spots. The neutralizer was added to the plates immediately after wiping to stop the species reaction with spores and to recover the spores. As shown in table below, the EtOH wipe with little or no EtOH to activate (lower concentrations) resulted in approximately 0.75 to 1.88 Log Reduction (LR) in colony forming units (CFU). The Log Reduction was mainly attributed to mechanical removal. The addition of EtOH to the wipe at concentration levels between 1.5% and 50% with showed approximately 3 LR to 4 LR, which was attributed to the combination of mechanical removal and chemical inactivation of the spores.

In another experiment, a 3 cm×3 cm Rubbermaid HYGEN™ microfiber wipe was wetted with different amounts of 70% (w/w) ethanol (EtOH) in the range of 80 µl to 500 µl. The EtOH-wetted wipes were activated by the indirect DBD for 45 seconds. After plasma activation, the activated wipes were immediately used to wipe the spore spots. The neutralizer was added to the plates immediately after wiping to stop the species reaction with spores and to recover the spores. As shown in the table below, increasing the volume of EtOH (70%) in the wipes decreased the efficacy of the wipes in reducing the number of colony forming units. Data suggests that higher volumes of liquid in the wipe may require longer activation time to achieve sufficient amount of species in the wipe.

In another experiment, a 3 cm×3 cm Rubbermaid HYGEN™ microfiber wipe was wetted with 160 µl of 30% (w/w) ethanol (EtOH) having a pH in the range of 2 to 13. The EtOH-wetted wipes were activated by the indirect DBD for 45 seconds. After plasma activation, the activated wipes were immediately used to wipe the spore spots. The neutralizer was added to the plates immediately after wiping to stop the species reaction with spores and to recover the spores. As shown in table below, efficacy of the 30% EtOH wipe remained high with liquid pH from 2-12. Once, however, liquid pH was raised to 13, the efficacy of the wipe significantly decreased.

In another experiment, a sanitizing wipe (62% ethyl alcohol and <5% isopropanol alcohol) was compared to an Isopropanol (IPA) Hand Wipe (70% isopropanol alcohol). The wipes were activated by the indirect DBD for a duration in the range of 10 seconds to 60 seconds. After plasma activation, the activated wipes were immediately used to wipe the spore spots. After wiping, the liquid delivered from the wipes was allowed to sit on the plates (i.e. in contact with the spores) for 60 sec to show that the species in the liquid can continue to kill spores. After 60 seconds, the neutralizer was added to the plates to stop the species reaction with spores and to recover the spores. As shown in the table below, both wipes achieved approximately 6 LR with 15 seconds or greater plasma activation time and 60 seconds contact time. The addition of alcohol was shown to stabilize the sporicidal species, leading to prolonged (>1 min) sporicidal efficacy of the activated wipes.

In another experiment, a 3 cm×3 cm Rubbermaid HYGEN™ microfiber wipe was compared to a 3 cm×3 cm IPA wipe made by Zee Medical, Inc. The wetted with 160 µl of ethanol (EtOH) having a pH in the range of 2 to 13. The wipes were activated by the indirect DBD for a duration in the range of 0 seconds to 60 seconds. After plasma activation, the activated wipes were immediately used to wipe the spore spots. The neutralizer was added to the plates immediately after wiping to stop the species reaction with spores and to recover the spores. The plasma activated water wipes showed the same sporicidal efficacy as the water wipes without plasma activation (~0.7 LR is due to the mechanical removal, which means the plasma activated water wipe does not show significant sporicidal effect. Plasma activated IPA wipes showed sporicidal efficacy but plasma activated water wipes did not show sporicidal activity.

In another experiment, a 3 cm×3 cm IPA was activated by the indirect DBD for a duration in the range of 0 seconds to 120 seconds. After plasma activation, the activated wipes were immediately used to wipe the spore spots or were allowed to sit in ambient air conditions for 60, 120, and 180 sec before wiping. The neutralizer was added to the plates immediately after wiping to stop the species reaction with spores and to recover the spores. The plasma-activated IPA wipes with 45 and 60 seconds plasma activation time achieved >4.5 LR. A plasma activation time greater than 100 seconds (e.g., 120 seconds) led to lower efficacy which may be attributed to drying of the wetted wipe. With a 45 second activation time, efficacy decreased when the wait time before wiping increased. The plasma activated IPA wipes continued to show good efficacy with 60 seconds wait time.

In another experiment, a 3 cm×3 cm 70% IPA wipe made by Zee Medical, Inc. was activated by the indirect DBD for zero seconds, 30 seconds, and 45 seconds. After plasma activation, the activated wipes were immediately used to wipe the spore spots. After wiping, the liquid delivered from the wipes was allowed to sit on the plates (i.e. in contact with the spores) for zero, 30 seconds and 60 seconds to show that the species in the liquid can continue to kill spores. The neutralizer was added to the plates to stop the species reaction with spores and to recover the spores. As shown in table below, >4.5 LR (CFU) against C. diff spores was achieved using plasma-activated IPA wipes with 30 seconds or 45 seconds plasma activation time plus 30 seconds or 60 seconds liquid contact time.

In another experiment, a Sanitizing Hand Wipes (0.1% Benzalkonium Chloride, 0.2% Glycerin, 0.75% Decyl Glucoside, 0.05% methylparaben, 0.05% propylparaben, and 0.4% phenoxyethanol in a polypropylene wipe) were activated by the indirect DBD for a duration in the range of 0 seconds to 60 seconds. After plasma activation, the activated wipes were immediately used to wipe the spore spots. The neutralizer was added to the plates immediately after wiping to stop the species reaction with spores and to recover the spores. As shown in table below, approximately 4 LR against C. diff spores was achieved using the plasma-activated benzalkonium chloride wipes with 45 sec plasma activation time.

In another experiment, a BAK Sanitizing Hand Wipes (0.1% Benzalkonium Chloride, 0.2% Glycerin, 0.75% Decyl Glucoside, 0.05% methylparaben, 0.05% propylparaben, and 0.4% phenoxyethanol in a polypropylene wipe) a Sanitizing Hand Wipe (62% ethyl alcohol and <5% isopropanol alcohol), an Isopropanol (IPA) Hand Wipe (70% isopropanol alcohol), a microfiber wipe wetted with 70% (w/w) ethanol (EtOH), and a Bleach wipe were compared. The wipes, except for the bleach wipe, were used to wipe a glass petri dish either without plasma activation or after being activated by the indirect DBD for 45 seconds. The bleach wipe was used to wipe a glass petri dish directly without plasma activation. After wiping, the liquid in the petri dish was allowed to dry and images of the petri dish were taken to record the amount of streaking on the glass. No residue (streaks) was observed with any of the wipes except for the Clorox bleach wipe, which showed heavy residue (streaks).

While the present invention has been illustrated by the description of embodiments thereof and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and/or illustrative examples shown and described. Accordingly, departures may be made from such details without departing from the spirit or scope of the applicants' general inventive concept.

We claim:

1. A dispenser system for generating and dispensing one or more wet wipes that have antimicrobial properties; comprising:
a dispenser housing having an opening;
a supply of one or more wipes disposed within the dispenser housing;
a non-thermal plasma generator disposed within the dispenser housing;
a power supply electrically coupled to the non-thermal plasma generator;
a reservoir for holding a supply of water or water with one or more additives located within the dispenser housing;
the supply of the water or water with one or more additives located in the reservoir;
wherein the water or water with one or more additives has properties that change when contacted by non-thermal plasma such that the water or water with one or more additives after being contacted by the non-thermal plasma non becomes activated water or activated water with one or more additives that contains one or more of ozone, hydrogen peroxide, nitrates, nitrites, peroxynitrious add, peroxynitrite, hydroxyl radicals or other active species;
wherein the power supply is configured to provide power to the non-thermal plasma generator to generate the non-thermal plasma;
wherein the non-thermal plasma generator is positioned in a location configured so that the non-thermal plasma generated from the non-thermal plasma generator contacts the water or water with one or more additives;
wherein the one or more wipes are impregnated with one of the water or water with one or more additives or one of the activated water or activated water with one or more additives to become the one or more wet wipes;
wherein if the one or more wet wipes are impregnated with the water or water with one or more additives, the non-thermal plasma generated by the non-thermal plasma generator contacts the one or more wet wipes and the water or water with one or more additives; and
a feed system disposed within the dispenser housing, wherein the feed system moves the one or more wipes wetted with the activated water or activated water with one or more additives out of the opening;
wherein the one or more wet wipes dispensed contain the one or more of ozone, hydrogen peroxide, nitrates, nitrites, peroxynitrious acid, peroxynitrite, hydroxyl radicals or other active species when dispensed out of the opening in the housing.

2. The dispenser system of claim 1 wherein the one or more wipes are pre-moistened with the supply of the water or water with one or more additives prior to being placed within the housing.

3. The dispenser system claim of 1 wherein the supply of the one or more wipes is a roll of the one or more wipes.

4. The dispenser system of claim 1 further comprising one or more nozzles fluidly coupled to the supply of the water or water with one or more additives and disposed within the dispenser housing, wherein the one or more nozzles are arranged to spray the water or water and one or more additives onto the one or more wipes to moisten the one or more wipes.

5. The dispenser system of claim 4 wherein the one or more nozzles are positioned to spray the activated water or activated water with one or more additives onto the one or more wipes after the plasma generator applies the non-thermal plasma to the water or water with one or more additives to generate the activated water or activated water with one or more additives.

6. The dispenser system of claim 4 wherein the one or more nozzles are positioned to spray the water or water with one or more additives onto the one or more wipes before the non-thermal plasma generator applies the non-thermal plasma to the one or more wipes.

7. The dispenser system of claim 1 further comprising a sensor that senses a condition of the one or more wipes, and wherein the system discontinues applying the non-thermal plasma to the one or more wipes when the sensed condition reaches a threshold value.

8. A dispenser system for generating one or more wipes having antimicrobial properties, comprising:
a dispenser housing having an opening;
a non-thermal plasma generator disposed within the dispenser housing;
a power supply electrically coupled to the non-thermal plasma generator;
one or more wet wipes;
wherein the one or more wet wipes contain a water or water with one or more additives;
wherein the water or water with one or more additives is liquid that has properties that change when contacted by non-thermal plasma such that the water or water with one or more additives after being contacted by the non-thermal plasma contains one or more of ozone, hydrogen peroxide, nitrates, nitrites, peroxynitrious acid, peroxynitrite, hydroxyl radicals or other active species;
wherein the non-thermal plasma generator is positioned proximate the one or more wet wipes and is configured so that the non-thermal plasma generated from the non-thermal plasma generator contacts the one or more wet wipes for a period of time to activate the water or water with one or more additives so that the water or water with one or more additives contain the one or more of ozone, hydrogen peroxide, nitrates, nitrites, peroxynitrious acid, peroxynitrite, hydroxyl radicals or other active species; and
wherein the dispenser system has a dispense mechanism to dispense the one or more wet wipes that contains the one or more of ozone, hydrogen peroxide, nitrates, nitrites, peroxynitrious add, peroxynitrite, hydroxyl radicals or other active species out of the dispenser housing.

9. The dispenser system of claim 8 further comprising a timer.

10. The dispenser system of claim 9 wherein the timer is used to determine the length of time to apply the non-thermal plasma to the one or more wet wipes.

11. The dispenser system of claim 9 wherein the timer is used to alert a user to status of the one or more wet wipes.

12. The dispenser system of claim 11 wherein the status of the one or more wet wipes is indicative of the efficacy of the one or more wet wipes.

13. The dispenser system of claim 12 wherein the status of the one or more wet wipes is the one or more wet wipes have sufficient antimicrobial or sporicidal activity.

14. A wet wipes dispensing device for dispensing wet wipes having antimicrobial or sporicidal properties comprising:
a dispenser housing;
a reservoir;
a supply of water or water with one or more additives located within the reservoir;
wherein the water or water with one or more additives have properties that change when contacted by non-thermal plasma such that the water or water with one or more additives after being contacted by the non-thermal plasma contains one or more of ozone, hydrogen peroxide, nitrates, nitrites, peroxynitrious acid, peroxynitrite, hydroxyl radicals or other active species;
a plurality of wipes located within the dispenser housing;
a non-thermal plasma generator;
wherein the non-thermal plasma generator is positioned close to at least a portion of the water or water with one or more additives from the supply of the water or water with one or more additives and is configured so that the non-thermal plasma generated by the non-thermal plasma generator will contact the at least a portion of the water or water with one or more additives used to wet one or more of the plurality of wipes;
a power supply configured for providing power to the non-thermal plasma generator to cause the non-thermal plasma generator to generate the non-thermal plasma proximate the at least a portion of the water or water with one or more additives from the supply of the water or water with one or more additives;
wherein upon contact of the at least a portion of the water or water with one or more additives with the non-thermal plasma, the at least a portion of the water or water with one or more additives is changed to the one or more of ozone, hydrogen peroxide, nitrates, nitrites, peroxynitrious acid, peroxynitrite, hydroxyl radicals or other active species; and
wherein the dispenser system is configured to impregnate the one or more of the plurality of wipes with the at least a portion of the water or water and one or more additives that contains the one or more of ozone, hydrogen peroxide, nitrates, nitrites, peroxynitrious acid, peroxynitrite, hydroxyl radicals or other active species; and
a feeder for dispensing the one or more of the plurality of wet wipes from the dispenser housing.

15. The device of claim 14 wherein the water with one or more additives comprises water and an additive.

16. The device of claim 15 wherein the additive is a stabilizer.

17. The device of claim 15 wherein the additive is an antimicrobial.

18. The device of claim 15 wherein the additive is an alcohol.

19. The device of claim 18 wherein the alcohol is ethanol.

20. The device of claim 16 wherein the at least a portion of the water or water with one or more additives is applied to the wipe prior to the fluid being in proximity of the non-thermal plasma generator to cause the at least a portion of the water or water with one or more additives to have antimicrobial activity.

* * * * *